(12) United States Patent
Lang et al.

(10) Patent No.: US 9,598,710 B2
(45) Date of Patent: *Mar. 21, 2017

(54) GENETICALLY MODIFIED ORGANISM FOR THE PRODUCTION OF LIPIDS

(71) Applicants: Christine Lang, Berlin (DE); Andreas Raab, Berlin (DE)

(72) Inventors: Christine Lang, Berlin (DE); Andreas Raab, Berlin (DE)

(73) Assignee: ORGANOBALANCE GMBH, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/491,212

(22) Filed: Sep. 19, 2014

(65) Prior Publication Data

US 2015/0024009 A1 Jan. 22, 2015

Related U.S. Application Data

(62) Division of application No. 13/392,601, filed as application No. PCT/EP2010/004925 on Aug. 4, 2010, now Pat. No. 8,841,114.

(30) Foreign Application Priority Data

Aug. 26, 2009 (EP) ..................................... 09075393

(51) Int. Cl.

| C12N 15/81 | (2006.01) |
|---|---|
| C12P 7/64 | (2006.01) |
| A61K 8/99 | (2006.01) |
| A61Q 19/00 | (2006.01) |
| C12N 9/02 | (2006.01) |
| C12N 9/10 | (2006.01) |
| C12P 5/00 | (2006.01) |
| C12P 33/00 | (2006.01) |
| C12N 9/04 | (2006.01) |

(52) U.S. Cl.

CPC .............. *C12P 7/6463* (2013.01); *A61K 8/99* (2013.01); *A61Q 19/00* (2013.01); *C12N 9/0006* (2013.01); *C12N 9/0071* (2013.01); *C12N 9/1007* (2013.01); *C12N 9/1029* (2013.01); *C12N 15/81* (2013.01); *C12P 5/007* (2013.01); *C12P 7/649* (2013.01); *C12P 7/6436* (2013.01); *C12P 33/00* (2013.01); *C12Y 101/01034* (2013.01); *C12Y 203/0102* (2013.01); *C12Y 203/01026* (2013.01); *Y02E 50/343* (2013.01); *Y02P 20/52* (2015.11)

(58) Field of Classification Search

CPC ........... C12N 15/81; C12P 7/64; C12P 7/6463
USPC ........................................................ 435/134
See application file for complete search history.

(56) References Cited

U.S. PATENT DOCUMENTS

| 5,349,126 | A | * | 9/1994 | Chappell | ............... | C12N 9/0006 |
|---|---|---|---|---|---|---|
| | | | | | | 435/69.1 |
| 5,460,949 | A | * | 10/1995 | Saunders | ............. | C12N 9/0006 |
| | | | | | | 435/189 |
| 6,153,424 | A | * | 11/2000 | Raymond | ............ | C12N 9/0006 |
| | | | | | | 435/219 |
| 6,190,914 | B1 | | 2/2001 | Grivell et al. | | |
| 6,730,499 | B1 | * | 5/2004 | Cregg | .................. | C12N 15/815 |
| | | | | | | 435/243 |
| 7,250,502 | B2 | * | 7/2007 | Cregg | .................. | C12N 15/815 |
| | | | | | | 435/243 |
| 7,745,200 | B2 | * | 6/2010 | Cregg | .................. | C12N 15/815 |
| | | | | | | 435/245 |
| 7,851,199 | B2 | * | 12/2010 | Bailey | ....................... | A23L 1/28 |
| | | | | | | 435/254.2 |
| 8,170,852 | B2 | * | 5/2012 | Famili | ..................... | G06F 19/12 |
| | | | | | | 702/19 |
| 8,288,149 | B2 | | 10/2012 | Bailey et al. | | |
| 8,367,395 | B2 | * | 2/2013 | Bailey | ................. | A23K 1/1612 |
| | | | | | | 435/183 |
| 8,841,114 | B2 | * | 9/2014 | Lang | ....................... | A61K 8/99 |
| | | | | | | 435/254.2 |

(Continued)

FOREIGN PATENT DOCUMENTS

| EP | 0486290 | | 5/1992 | | |
|---|---|---|---|---|---|
| EP | 0486290 | A2 * | 5/1992 | ............. | C12N 15/81 |

(Continued)

OTHER PUBLICATIONS

Arthington-Skaggs et al, FEBS Letters, vol. 392, pp. 161-165, 1996, Positive and negative regulation of a sterol biosynthetic gene (ERG3) in the post squalene portion of the yeast ergosterol pathway.*

(Continued)

*Primary Examiner* — Albert Navarro

(74) *Attorney, Agent, or Firm* — Ann Wieczorek; Mayer & Williams PC

(57) ABSTRACT

The invention provides an isolated genetically modified non-mammalian organism, wherein the activity of acyl-CoA:sterol acyltransferase/sterol O-acyltransferase (EC 2.3.1.26) and/or diacylglycerol acyltransferase/diacylglycerol O-acyltranferase (EC 2.3.1.20) and/or lecithin cholesterol acyl transferase/phospholipid:diacylglycerol acyltransferase (EC 2.3.1.158) and/or acyl CoA-wax alcohol acyltransferase (EC 2.3.1.75) is reduced or abolished in comparison with a corresponding wildtype organism, methods of use of such an organism, shuttle vehicles for making such an organism and methods for producing such an organism.

12 Claims, 4 Drawing Sheets

(56) References Cited

U.S. PATENT DOCUMENTS

| | | | |
|---|---|---|---|
| 2003/0215920 A1* | 11/2003 | Cregg | C12N 15/815 435/69.1 |
| 2003/0228567 A1* | 12/2003 | Famili | G06F 19/12 435/4 |
| 2005/0086718 A1 | 4/2005 | Heard et al. | |
| 2006/0263863 A1 | 11/2006 | Hahn et al. | |
| 2006/0263864 A1 | 11/2006 | Busby et al. | |
| 2008/0034453 A1 | 2/2008 | Cheikh et al. | |
| 2008/0261280 A1 | 10/2008 | Hahn et al. | |
| 2009/0298150 A1* | 12/2009 | Walker | C12P 5/007 435/167 |
| 2010/0297736 A1* | 11/2010 | Duhring | C12N 15/74 435/252.3 |
| 2010/0305341 A1* | 12/2010 | Bailey | A23K 1/1612 549/512 |
| 2011/0039316 A1 | 2/2011 | Onishi et al. | |
| 2011/0129885 A1 | 6/2011 | Lang et al. | |
| 2011/0243969 A1* | 10/2011 | Broeker | C12P 5/02 424/184.1 |
| 2012/0156695 A1 | 6/2012 | Schilling et al. | |
| 2012/0261568 A1 | 10/2012 | Coon et al. | |
| 2013/0031669 A1 | 1/2013 | Heard et al. | |
| 2013/0302861 A1* | 11/2013 | Vainstein | C12P 5/007 435/131 |
| 2014/0030795 A1 | 1/2014 | Donaldson et al. | |
| 2014/0256011 A1* | 9/2014 | Zelle | C12N 15/81 435/161 |
| 2014/0322771 A1* | 10/2014 | Yang | C12N 9/1007 435/134 |

FOREIGN PATENT DOCUMENTS

| | | | | |
|---|---|---|---|---|
| WO | 2006/102342 | * | 9/2006 | |
| WO | 2007/130423 | | 10/2007 | |
| WO | 2008/130372 | * | 10/2008 | C12N 1/00 |

OTHER PUBLICATIONS

Casey, Warren M. et al, Journal of Bacteriology, Nov. 1992, pp. 7283-7288, vol. 174(22), Regulation of Partitioned Sterol Biosynthesis in *Saccharomyces cerevisiae*.*

Johnson, Monique A et al, Genetics vol. 151, pp. 1379-1391, Apr. 1999.*

Gachotte, D et al, Characterization of the *Saccharomyces cerevisiae* ERG27 gene encoding 3-keta reductase involved in C-4 sterol demethylation, PNAS, Oct. 26, 1999, vol. 96(22), pp. 12655-12660.*

Donald, K. Allen G. et al, Applied and Environmental Microbiology, Sep. 1997, pp. 3341-3344, vol. 63(9), Effects of Overproduction of the catalytic Domain of 3-hydroxy-3-methylglutaryl Coenzyme A Reductase on Squalene Synthesis in *Saccharomyces cerevisiae*.*

Asadollahi, MA et al, Biotechnology and Bioengineering, Production of Plant Sesquiterpenes in *Saccharomyces cerevisiae*: Effect of ERG9 Repression on Sesquiterpene Biosynthesis, published online Aug. 17, 2007, vol. 99(3), Feb. 15, 2008.*

Fei, W et al, Fld1p, a functional homologue of human seipin, regulates the size of lipid droplets in yeast, Published on line Feb. 4, 2008, Journal of Cell Biology, vol. 180(3), pp. 473-482, Feb. 11, 2008.*

Jensen-Pergakes, et al., "Transcriptional Regulation of the Two Sterol Esterification Genes in the Yeast *Saccharomyces cerevisiae*", Journal of Bacteriology, Sep. 2001, pp. 4950-4957.

Polakowski et al. "Overexpression of a cytosolic hydroxymethylglutaryl-CoA reductase leads to squalene accumulation in yeast", Appl Microbiol Biotechnol (1998) 49: 66-71.

Donald et al. "Effects of Overproduction of the Catalytic Domain of 3-Hydroxy-3-Methylglutaryl Coenzyme A Reductase on Squalene Synthesis in *Saccharomyces cerevisiae*", Applied and Environmental Microbiology, Sep. 1997, pp. 3341-3344.

Daum et al., "Dynamics of neutral lipid storage and mobilization in yeast", Biochimie 89 (2007) 243-248.

Dimster-Denk et al., "Comprehensive evaluation of isoprenoid biosynthesis regulation in *Saccharomyces cerevisiae* utilizing the Genome Reporter Matrix", Journal of Lipid Research vol. 40, 1999, pp. 850-860.

Boll et al. "Effect of Unsaturated Fatty Acids of Sterol Biosynthesis in Yeast", Biochimica et Biophysicsa Acta. 620 (1980) 429-439.

Frederick, DL et al. Molecular and Cellular Biology, 1996, vol. 16(6), pp. 2922-2931, "The REG2 Gene of *Saccharomyces cerevisiae* Encodes a Type I protein phosphatase-Binding protein that functions with Reg1p and the Snf1 Protein kinases to Regulate growth."

Steinberg, Gregory R. et al. Physiology Review, vol. 89, pp. 1025-1078, 2009, AMPK in Health and Disease.

Hovland, PG et al., Molecular and General Genetics, 1997, vol. 256, pp. 45-53, Overexpression of the protein kinase Pak1 surpresses yeast DNA polymerase mutations.

Schaller, Hubert et al., Plant Physiology, 1995, vol. 109, pp. 761-770, Expression of the Heve Brasiliensis (H.B.K.) Mull. Arg. 3-hydroxy-2-methylglutaryl-coenzyme A. Reductase 1 in Tobacco Results in Sterol Overproduction.

Fei W. et al., The Journal of Cell Biology, Feb. 4, 2008, Fld1p, a functional homologue of human seipin, regulates the size of lipid droplets in yeast, pp. 473-482, vol. 180(3) (Feb. 11, 2008).

* cited by examiner

```
ATGGACCAATTGGTGAAAACTGAAGTCACCAAG
AAGTCTTTTACTGCTCCTGTACAAAAGGCTTCTACACCAGTTTTAACCAATAAAACAGTC
ATTTCTGGATCGAAAGTCAAAAGTTTATCATCTGCGCAATCGAGCTCATCAGGACCTTCA
TCATCTAGTGAGGAAGATGATTCCCGCGATATTGAAAGCTTGGATAAGAAAATACGTCCT
TTAGAAGAATTAGAAGCATTATTAAGTAGTGGAAATACAAAACAATTGAAGAACAAAGAG
GTCGCTGCCTTGGTTATTCACGGTAAGTTACCTTTGTACGCTTTGGAGAAAAAATTAGGT
GATACTACGAGAGCGGTTGCGGTACGTAGGAAGGCTCTTTCAATTTTGGCAGAAGCTCCT
GTATTAGCATCTGATCGTTTACCATATAAAAATTATGACTACGACCGCGTATTTGGCGCT
TGTTGTGAAATGTTATAGGTTACATGCCTTTGCCCGTTGGTGTTATAGGCCCCTTGGTT
ATCGATGGTACATCTTATCATATACCAATGGCAACTACAGAGGGTTGTTTGGTAGCTTCT
GCCATGCGTGGCTGTAAGGCAATCAATGCTGGCGGTGGTGCAACAACTGTTTTAACTAAG
GATGGTATGACAAGAGGCCCAGTAGTCCGTTTCCCAACTTTGAAAAGATCTGGTGCCTGT
AAGATATGGTTAGACTCAGAAGAGGGACAAAACGCAATTAAAAAAGCTTTTAACTCTACA
TCAAGATTTGCACGTCTGCAACATATTCAAACTTGTCTAGCAGGAGATTTACTCTTCATG
AGATTTAGAACAACTACTGGTGACGCAATGGGTATGAATATGATTTCTAAAGGTGTCGAA
TACTCATTAAAGCAAATGGTAGAAGAGTATGGCTGGGAAGATATGGAGGTTGTCTCCGTT
TCTGGTAACTACTGTACCGACAAAAAACCAGCTGCCATCAACTGGATCGAAGGTCGTGGT
AAGAGTGTCGTCGCAGAAGCTACTATTCCTGGTGATGTTGTCAGAAAAGTGTTAAAAAGT
GATGTTTCCGCATTGGTTGAGTTGAACATTGCTAAGAATTTGGTTGGATCTGCAATGGCT
GGGTCTGTTGGTGGATTTAACGCACATGCAGCTAATTTAGTGACAGCTGTTTTCTTGGCA
TTAGGACAAGATCCTGCACAAAATGTTGAAAGTTCCAACTGTATAACATTGATGAAAGAA
GTGGACGGTGATTTGAGAATTTCCGTATCCATGCCATCCATCGAAGTAGGTACCATCGGT
GGTGGTACTGTTCTAGAACCACAAGGTGCCATGTTGGACTTATTAGGTGTAAGAGGCCCG
CATGCTACCGCTCCTGGTACCAACGCACGTCAATTAGCAAGAATAGTTGCCTGTGCCGTC
TTGGCAGGTGAATTATCCTTATGTGCTGCCCTAGCAGCCGGCCATTTGGTTCAAAGTCAT
ATGACCCACAACAGGAAACCTGCTGAACCAACAAAACCTAACAATTTGGACGCCACTGAT
ATAAATCGTTTGAAAGATGGGTCCGTCACCTGCATTAAATCCTAA
```

Figure 5

GENETICALLY MODIFIED ORGANISM FOR THE PRODUCTION OF LIPIDS

FIELD OF THE INVENTION

The invention is directed to genetically modified non-mammalian organisms, in particular microorganisms, wherein certain enzymatic activities are decreased and/or increased, which are useful in the industrial biosynthesis of lipids, in particular neutral lipids. The invention further relates to uses of such organisms, shuttle vehicles for making such organisms and methods for the production of such organisms.

BACKGROUND OF THE INVENTION AND STATE OF THE ART

Lipids are hydrophobic or amphipathic small molecules that originate entirely or in part by carbanion-based condensations of thioesters like fatty acids or polyketides and/or by carbocation-based condensations of isoprene units like prenols or sterols. This group comprises several substances of high economical importance. The group of the triacylglycerol-lipids comprises, for example, oils, fats or waxes, which are used in a vast variety of contexts, e.g. as ingredients in food or for cooking, to make soaps, skin products, perfumes and other personal care and cosmetic products, for making paints and other wood treatment products, as biodegradable insulators in the electrical industry, to produce bio-degradable hydraulic fluids, as lubricants, or even as the basis of biodiesel, which can be used to substitute conventional diesel. The isoprenoid-lipid squalene is, for instance, used as an adjuvant in vaccines or other pharmaceuticals, nutrients, cosmetics as well as over-the-counter drugs. Squalene can also be used as a building block for the synthesis of terpenes. Furthermore squalene can industrially be used as biodegradable lubricant. Other economically important lipids are sterols like ergosterol, zymosterol, episterol, 7-dehydrocholesterol or lanosterol, which are utilized as pivotal starting material for the production of compounds like saponin, steroid hormones, vitamins and pharmaceutical substances.

Lipids, in particular neutral lipids, are normally stored in the cell in specific intracellular organelles known as lipid particles. These particles are characterized by a simple structure consisting of a highly hydrophobic monolayer with only a small amount of proteins embedded. The lipids are stored in the lipid particles until hydrolysis directs return of their components to metabolic and/or catabolic pathways. This process of lipid depot formation is widely used in nature, and all types of eukaryotic cells contain intracellular lipid particles, which can also be called lipid bodies, lipid droplets, oil bodies or oleosomes. In the yeast *Saccharomyces cerevisiae* lipid droplets accumulate up to 70% of the total lipid content of the cell.

Since most of the mentioned lipids are derivable from natural sources like plants, animals or microorganisms, attempts were made to increase the lipid amount in the living cells, i.e. to accumulate more lipids in the lipid particles. For this purpose it is known to modify the metabolic pathways of organisms. The document EP-0 486 290 A describes the over-expression of genes of the ergosterol metabolism in yeast resulting in an increase of the amount of ergosterol in the cells. The document WO03/064652 A discloses a method for the production of zymosterol based on the increase of lanosterol-C14-demethylase and HMG-CoA-reductase activity. In the document WO2004/083407 A transgenic organisms are described, which have a reduced Δ22-desaturase activity and an increased activity of HMG-CoA reductase, lanosterol C14-demethylase, squalene epoxidase and squalene synthetase. These organisms can be used for the production of the sterol lipid ergosta-5,7-dienol. Thus, by biologically modifying lipid generating organisms the yield of the produced lipids can be significantly increased.

However, the obtained lipid compounds are mostly unpure and intermingled and need to be separated and/or purified, in particular if the lipid is to be used as a starting material for further chemical syntheses or modifications. In addition, any purification procedure, especially if it is carried out on an industrial scale, is expensive, laborious and tends to pollute the environment.

Technical Problem of the Invention

Accordingly, the technical problem underlying the instant invention comprises to provide means and methods allowing the production of lipids by organisms in a more pure form in order to avoid laborious and cost intensive purification procedures.

SUMMARY OF THE INVENTION AND PREFERRED EMBODIMENTS

In order to solve this technical problem, the instant invention teaches an organism according to claim 1. Preferred embodiments are specified in the claims dependent on claim 1. Therein the phrase "genetically modified" is intended to comprise not only organisms, wherein the genom has been modified by state of the art methods of genetic engineering, but also organisms, which have been selected from a mutant group according to the desired genetic modification (conventional mutagenesis).

The invention is based on the finding that it is possible to genetically engineer or biochemically modify organisms so that specific (neutral) lipids are accumulated in lipid particles in a more pure form. The organisms of the invention are modified in a way which eliminates or reduces the synthesis of not desired steryl acyl esters and/or of triacylglycerols and/or of wax esters depending on the lipid which is intended to be produced by the organism in higher purity. Besides the accumulation of a neutral lipid in a more pure form, the reduction or the elimination of the potentially contaminating steryl acyl esters and/or of triacylglycerols and/or of wax esters also surprisingly leads to increased levels and yields of the desired lipid. This might be due, without being bound to this theory, to the increased storage space in the lipid particles and/or due to the increased availability of substrate for the synthesis of the desired lipid.

The term "neutral lipid" relates to lipids which lack charged groups and are therefore unable to integrate into bilayer membranes in substantial amounts. The term comprises triacylglycerols (TAGs), sterylacyl esters (SAEs) and wax esters (WEs). Squalene also belongs to the class of "neutral lipids". Normally, the content of the lipid particle is a mixture of different neutral lipids which hampers an efficient production of a desired specific neutral lipid in a recombinant organism. This problem is overcome by the present invention by modifying a producer organism such that at least one type of neutral lipid which naturally occurs in said organism in said lipid article is no longer synthesized thereby. As a result, the composition of the remaining neutral lipids contained in the lipid particle becomes purer and thus more attractive for the production for commercial purposes.

Generally, any single activity or combination of different activities (two, three or four) according to claim 1 can be employed, depending on the neutral lipid, which is intended to be synthesized in higher purity, or, in turn, depending on the neutral lipid, which is intended to be removed in the biosynthesis as an unwanted contaminant. Thus, various embodiments of the invention exist and only some specific embodiments will be described in the following in more detail.

Thus, in a first embodiment, the organism according to the present invention is modified so that it no longer synthesizes a steryl acyl ester (SAE). Steryl acyl esters are esters of sterols with long chain fatty acids. Generally, synthesis of SAEs is accomplished in the cells by an enzymatic mechanism involving acyl-CoA:sterol acyl transferase/sterol O-acyltransferase (EC 2.3.1.26). The catalysed reaction is the esterification of sterols with long chain fatty acids. Thus, in a preferred embodiment, the organism according to the present invention is modified so that the activity of the acyl-CoA:sterol acyltransferase/sterol O-acyltransferase (EC 2.3.1.26) is reduced in comparison to a corresponding non-modified organism, preferably a corresponding wildtype organism.

In yeast, in particular in *S. cerevisiae*, sterol esterification to yield steryl acyl esters is accomplished by two isoenzymes of the steryl acyl transferase, i.e. Are1p and Are2p, which have different specific affinities for different sterol intermediates. Are1p leads in particular to the esterification of ergosterol precursors such as lanosterol, zymosterol, ergosta-5,7-dienol and substances foreign to yeast such as 7-dehydro cholesterol. Are2p leads preferentially to the esterification of ergosterol, the end product of the ergosterol biosynthesis pathway in yeast. If the organism is a yeast organism, in particular of the genus *Saccharomyces* and preferably *S. cerevisiae*, the activity of Are1p or of Are2p or of both, Are1p and Are2p, may be reduced or abolished in comparison to a corresponding non-modified yeast organism, preferably a corresponding wildtype organism. If both enzyme activities are eliminated, no esterification of sterols occurs in the cells. By only eliminating one activity and maintaining the other it is possible to obtain, if desired, a certain type of steryl acyl ester in the cells if the enzyme activities leading to a certain sterol are accordingly maintained or adapted in the organism.

In connection with the first aspect of the invention in which the organism is characterized in that it does no longer synthesize a steryl acyl ester, the organism according to the invention may in principle be any possible organism, a plant organism, a fungal organism or a bacterial organism. However, preferably the organism is derived from an organism which does naturally not store wax esters in its lipid particles but only other lipids like triacylglycerols and steryl acyl esters. Thus, by eliminating the biosynthetic pathway for the synthesis of steryl acyl ester, such an organism accumulates in its lipid particles basically only triacylglycerols thereby allowing to produce in such an organism triacylgylcerols in rather pure form from the lipid particles. Examples for organisms which do naturally not accumulate wax esters in their lipid particles are in particular most animals, fungal cells and most plant cells except for algae and plankton cells. In a particularly preferred embodiment in connection with the first aspect of the present invention, the organism is a fungal organism, preferably a fungal organism of a genus selected from the group consisting of *Yarrowia, Rhodotorula, Lipomyces, Candida, Rhodosporidium, Mortierella, Mucor, Saccharomyces, Pichia, Kluyveromyces, Aspergillus, Penicillium* and *Dictyostelium*. Particularly preferred are fungal organisms of the species *Yarrowia lipolytica, Rhodotorula glutinis, Lipomyces starkeyi, Candida curvata, Rhodosporidium tortuloides, Mortierella isabellina, Mucor javonicus, Saccharomyces cerevisiae, Pichia pastoris, Kluyveromyces* spec., *Aspergillus* spec., *Penicillium* spec. or *Dictyostelium* spec. In a particularly preferred embodiment of the first aspect of the invention the organism is *S. cerevisiae*.

In a second embodiment, the organism according to the present invention is modified so that it no longer synthesizes a steryl acyl ester (SAE) and a wax ester (WE). Generally, the synthesis of WEs is accomplished in the cells by an enzymatic mechanism involving acyl CoA-wax alcohol acyltransferase (EC 2.3.1.75). Thus, in a preferred embodiment of the second aspect of the present invention, the organism according to the present invention is modified such that the activity of the acyl-CoA:sterol acyltransferase/sterol O-acyltransferase (EC 2.3.1.26) and of acyl CoA-wax alcohol acyltransferase (EC 2.3.1.75) is reduced in comparison to a corresponding non-modified organism, preferably a corresponding wildtype organism.

The organism according to the present invention in connection with the second aspect of the invention accumulates in the lipid particles predominantly triacylglycerols since the synthesis of steryl acyl esters and wax esters is reduced, preferably completely eliminated. Such organisms are therefore suitable to produce, in particular on an industrial scale, triacylglycerols in a purer form.

The organism according to the second aspect of the present invention is, preferably, derived from an organism which naturally produces wax esters and stores them intracellularly in lipid particles. Organisms which produce and store wax esters are, e.g. plants and insects in which they are used to provide the hydrophobic coating of tissues to minimize dehydration of surfaces, algae, plankton organisms and bacteria. In a preferred embodiment of the second aspect of the present invention, the organism is a bacterial organism, preferably of the genus *Mycobacterium, Streptomyces, Rhodococcus, Nocardia, Bacillus, Corynebacterium, Escherichia* or *Lactobacillus*. Most preferably the organism is *Escherichia coli*.

Moreover, it is not only possible to produce in such an organism according to the present invention triacylglycerols which are naturally produced in the organism or in an amount in which they are naturally produced in the organism but it is also possible to genetically modify such an organism to increase the amount of one or more particular triacylglycerols naturally produced in said organism or to genetically modify such an organism so as to lead to the synthesis of one or more triacylglycerols which is/are naturally not produced by such an organism.

In a particularly preferred embodiment the triacylglycerol accumulated by the organism according to the invention is an ester of glycerol and at least one unsaturated fatty acid and more preferably said unsaturated fatty acid is an omega-3 fatty acid. In principle, said omega-3 fatty acid can be any possible omega-3 fatty acid, but preferably it is α-linolenic acid (ALA), stearidonic acid, eicosatetraenoic acid, eicosapentaenoic acid (EPA), docosapentaenoic acid (DPA) or docosahexaenoic acid (DHA).

In another preferred embodiment the unsaturated fatty acid in the triacylglycerol is an omega-6 fatty acid. In principle, said omega-6 fatty acid can be any possible omega-6 fatty acid, but preferably it is linoleic acid, gamma-linolenic acid, eicosadienoic acid, dihomo-gamma-linolenic acid, arachidonic acid, docosadienoic acid, adrenic acid, docosapentaenoic acid or calendic acid.

In another preferred embodiment the unsaturated fatty acid in the triacylglycerol is an omega-9 fatty acid. In principle, the omega-9 fatty acid can be any possible omega-9 fatty acid, but preferably it is oleic acid, eicosenoic acid, mead acid, erucic acid or nervonic acid.

The first and the second embodiment may be further improved, as described in the following. Triacylglycerols are generally formed by the esterification of diacylglycerol with long chain fatty acids or phospholipids. The esterification with long chain fatty acids is catalyzed by diacylglycerol acyltransferase/diacylglycerol O-acyltransferase (EC 2.3.1.20). The esterification with phospholipids is catalyzed by lecithin cholesterol acyl transferase/phospholipid:diacylglycerol acyltransferase (EC 2.3.1.158). In a particularly preferred embodiment the organism according to the first or second aspect of the present invention is characterized in that the activity of diacylglycerol acyltransferase/diacylglycerol O-acyltranferase (EC 2.3.1.20) and/or the activity of lecithin cholesterol acyl transferase/phospholipid:diacylglycerol acyltransferase (EC 2.3.1.158) is increased in comparison with a corresponding non-modified organism, preferably a corresponding wildtype organism. The increase in activity of one or both of the two above mentioned enzymes leads to an increase in the synthesis of TAGs in the cells of the organism.

Apart from this, it is also possible to genetically modify the organism so as to enable the organism to produce certain fatty acids to be incorporated into the TGAs or to increase the production of such fatty acids if they are already naturally produced in such an organism in order to increase their content in the TGAs produced in said organism. For example, if it is intended to increase in the TGAs produced in the organism the amount of omega-3 fatty acids, such as eicosapentaenoic acid (EPA), docosapentaenoic acid (DPA) and/or docosahexanoic acid (DHA) it would be advantageous to increase the following enzymatic activities: Δ12 fatty acid desaturase (EC 1.14.19), Δ15-desaturase (EC 1.14.19), Δ6 fatty acid desaturase (EC 1.14.19.3), fatty acid elongase, Δ5-desaturase/Δ5-fatty acid desaturase (EC 1.14.19) and Δ4 fatty acid desaturase (EC 1.14.19). Thus, in a preferred embodiment the organis is characterized in that the activity of diacylglycerol acyltransferase/diacylglycerol O-acyltranferase (EC 2.3.1.20) and/or lecithin cholesterol acyl transferase/phospholipid:diacylglycerol acyltransferase (EC 2.3.1.158) and at least one of the activities selected from the group consisting of Δ12 fatty acid desaturase (EC 1.14.19), Δ15-desaturase (EC 1.14.19), Δ6 fatty acid desaturase (EC 1.14.19.3), fatty acid elongase, Δ5-desaturase/Δ5-fatty acid desaturase (EC 1.14.19) and Δ4 fatty acid desaturase (EC 1.14.19) is increased in comparison with a corresponding non-modified organism, preferably a corresponding wildtype organism. For example, plants and some fungi are capable of producing omega-3 and omega-6 fatty acids whereas, e.g., Saccharomyces cerevisiae can only synthesize omega-9 fatty acids. Thus, if the organism according to the invention is Saccharomyces cerevisiae, it may be desirable to introduce into the cells those enzyme activities which are necessary to produce omega-3 and/or omega-6 fatty acids. Approaches to introduce corresponding genes into yeast cells have already been described in the literature as well as the corresponding genes (see, e.g., WO2004/101575). The heterologous biosynthesis of specific fatty acids, e.g. in yeast cells is, for example described in Beaudoin et al. (Proc. Natl. Acad. Sci. USA 97 (2000), 6421-6426) and in Veen et al. (Appl. Microbiol. Biotechnol. 63 (2004), 635-646).

The present invention also relates to a method for producing a triacylglycerol comprising culturing the organism of the first or second aspect of the invention. As described above these organisms are capable of accumulating in their lipid particles large amounts of triacylglycerols in basically pure form. The TAGs can be isolated from the organisms according to methods well known in the art. It is, e.g., known in the art how to isolate lipid particles from cells and how to isolate from these the neutral lipids contained therein. An example for such a method is described for the organism Saccharomyces cerevisiae in the appended Examples.

The present invention also relates to a method for producing a triacylglycerol which is an ester of glycerol and at least one unsaturated fatty acid which comprises (i) the reduction or elimination by an inhibitor of the activity of acyl-CoA:sterol acyl-transferase/sterol O-acyltransferase (EC 2.3.1.26) and/or of acyl CoA-wax alcohol acyltransferase (EC 2.3.1.75); and (ii) increasing the activity of diacylglycerol acyltransferase/diacylglycerol O-acyltransferase (EC 2.3.1.20) and/or of lecithin cholesterol acyl transferase/phospholipid:diacylglycerol acyltransferase (EC 2.3.1.158)

in an organism in comparison to a corresponding non-modified organism, preferably a corresponding wild-type organism. The organism is cultured and the TAGs can be isolated.

As regards the unsaturated fatty acid(s) to be contained in the triacylglycerol to be produced, the same applies with respect to preferred embodiments what has already been described above regarding the nature of the polyunsaturated fatty acid(s) and of the enzyme activities to be increased. In a particularly preferred embodiment, the polyunsaturated fatty acid is an omega-3 fatty acid and the increased enzyme activity is at least one of those mentioned herein further above in connection with omega-3 fatty acids.

In a third embodiment, the organism according to the present invention is modified so that it no longer synthesizes a triacylglycerol (TAG) and a steryl acyl ester (SAE). As described above, generally synthesis of TAGs is accomplished by the enzymatic activities of diacylglycerol acyltransferase/diacylglycerol O-acyltranferase (EC 2.3.1.20) and lecithin cholesterol acyl transferase/phospholipid:diacylglycerol acyltransferase (EC 2.3.1.158). Thus, in a preferred embodiment, the organism according to the present invention is modified so that the activity of acyl-CoA:sterol acyltransferase/sterol O-acyltransferase (EC 2.3.1.26) of diacylglycerol acyltransferase/diacylglycerol O-acyltranferase (EC 2.3.1.20) and of lecithin cholesterol acyl transferase/phospholipid:diacylglycerol acyltransferase (EC 2.3.1.158) is reduced in comparison to a corresponding non-modified organism, preferably a corresponding wild-type organism.

In a preferred embodiment the organism according to the third aspect of the invention is an organism which is derived from an organism which naturally produces and stores wax esters. Such organisms are already described above. Preferably the organism is a bacterial organism as already described above, most preferably it is Escherichia coli. Due to the elimination of the synthesis of a TAG and of an SAE, such an organism would be suitable to predominantly accumulate in its lipid particles wax esters. In a particularly preferred embodiment such an organism is moreover characterized in that it shows an increase in the activity of acyl-CoA wax alcohol acyltransferase (EC 2.3.1.75) in comparison to a corresponding non-modified strain, preferably a corresponding wildtype strain. This would allow to increase the amount of wax esters synthesized in the organism. Means and methods for increasing the activity of a desired enzyme in the cells of an organism are known to the person skilled in the art and are described herein further below.

In another preferred embodiment the organism according to the third aspect of the invention is derived from an organism which naturally does not produce and store wax esters. Such organisms have been described above in connection with the first aspect of the invention. Preferably, such an organism is a fungal organism as described above, more preferably of the genus *Saccharomyces* and most preferably of the species *Saccharomyces cerevisiae*. Due to the elimination of the synthesis of a TAG and SAE, the lipid particles of such an organism can be used to accumulate a lipid of interest, e.g. squalene as is described further below.

In a fourth embodiment, the organism according to the present invention is modified so that it no longer synthesizes a wax ester (WE), a triacylglycerol (TAG) and a steryl acyl ester (SAEs). In this aspect the organism basically does not store any WEs, TAGs and SEs in its lipid particles. Such an organism is particularly useful for designing organisms into the lipid particles of which specifically desired lipids can be directed. It is, e.g. possible to introduce into such an organism nucleic acid molecules allowing the synthesis of another type of lipid which is then accumulated in the lipid particles. By this, organisms can be provided which allow the synthesis of basically pure desired lipids in the lipid particles.

In a preferred embodiment, the organism according to the fourth aspect of the present invention is modified so that the activity of acyl-CoA:sterol acyltransferase/sterol O-acyltransferase (EC 2.3.1.26) of diacylglycerol acyltransferase/diacylglycerol O-acyltranferase (EC 2.3.1.20), of lecithin cholesterol acyl transferase/phospholipid:diacylglycerol acyltransferase (EC 2.3.1.158) and of acyl CoA-wax alcohol acyltransferase (EC 2.3.1.75) is reduced in comparison to a corresponding non-modified organism, preferably a corresponding wildtype organism.

In a fifth embodiment, the organism according to the present invention is an organism which produces in the cell(s) a neutral lipid that is accumulated in a lipid particle and which is genetically modified so that it no longer synthesizes a triacylglycerol (TAG) and that therefore does no longer contain said triacylglycerol which naturally occurs in its lipid particles in said particles. As described above, generally synthesis of TAGs is accomplished, for example in yeast, by the enzymatic activities of diacylglycerol acyltransferase/diacylglycerol O-acyltranferase (EC 2.3.1.20) and lecithin cholesterol acyl transferase/phospholipid:diacylglycerol acyltransferase (EC 2.3.1.158). Thus, in a preferred embodiment, the organism according to the fifth aspect of the present invention is genetically modified so that the activity of diacylglycerol acyltransferase/diacylglycerol O-acyltranferase (EC 2.3.1.20) and of lecithin cholesterol acyl transferase/phospholipid:diacylglycerol acyltransferase (EC 2.3.1.158) is reduced in comparison to a corresponding non-modified organism, preferably a corresponding wildtype organism.

In a preferred embodiment of the fifth aspect of the present invention the organism is derived from an organism which naturally does not produce and store wax esters in its lipid particles. Such organisms have been described above. Preferably the organism is a fungal organism as described above, more preferably of the genus *Saccharomyces* and most preferably of the species *Saccharomyces cerevisiae*.

In a sixth embodiment, the organism according to the present invention is an organism which produces in the cell(s) a neutral lipid that is accumulated in a lipid particle and which is genetically modified so that it no longer synthesizes a wax ester (WE) and a triacylglycerols (TAG) and that therefore does no longer contain triacylglycerols and wax esters which naturally occur in its lipid particles in said particles. In a preferred embodiment, the organism according to the sixth aspect of the present invention is genetically modified so that the activity of diacylglycerol acyltransferase/diacylglycerol O-acyltranferase (EC 2.3.1.20), of lecithin cholesterol acyl transferase/phospholipid:diacylglycerol acyltransferase (EC 2.3.1.158) and of acyl CoA-wax alcohol acyltransferase (EC 2.3.1.75) is reduced in comparison to a corresponding non-modified organism, preferably a corresponding wildtype organism.

In a preferred embodiment the organism according to the fifth or sixth aspect of the present invention, i.e. an organism which does no longer synthesize a triacylglycerol or which does no longer synthesize a triacylglycerol and a wax ester, is capable of accumulating in its lipid particles an acyl ester of a sterol lipid. The accumulation of the acyl ester of a sterol lipid in the lipid particles may be due to the fact that the organism naturally synthesizes such esters or it may be due to the fact that genes encoding the corresponding enzymes leading to the biosynthesis of acyl esters of sterol lipids have been introduced into the cells.

Sterol lipids, such as cholesterol and its derivatives are important components of membrane lipids, along with the glycerophospholipids and sphingomyelins. The steroids, which also contain the same fused four-ring core structure, have different biological roles as hormones and signaling molecules. The C18 steroids include the estrogen family whereas the C19 steroids comprise the androgens such as testosterone and androsterone. The C21 subclass includes the progestogens as well as the glucocorticoids and mineralocorticoids. The secosteroids, comprising various forms of vitamin D, are characterized by cleavage of the B ring of the core structure. Other examples of sterols are the bile acids and their conjugates, which in mammals are oxidized derivatives of cholesterol and are synthesized in the liver.

In a preferred embodiment the sterol lipid is a sterol or a steroid. A steroid is a terpenoid lipid characterized by a carbon skeleton with four fused rings, generally arranged in a 6-6-6-5 fashion. Steroids vary by the functional groups attached to these rings and the oxidation state of the rings. Hundreds of distinct steroids are found in plants, animals and fungi. All steroids are made in cells either from the sterol lanosterol (animals and fungi) or the sterol cycloartenol (plants). Both sterols are derived from the cyclization of the triterpene squalene. Steroids include estrogen, progesterone and testosterone.

Sterols (or steroid alcohols) are a subgroup of steroids with a hydroxyl group in the 3-position of the A-ring. They are amphiphatic lipids synthesized from acetyl-conenzyme A. The overall molecule is quite flat. The hydroxyl group on the A ring is polar. The rest of the aliphatic chain is non-polar. Sterols of plants are called phytosterols and sterols of animals are called zoosterols. The most important zoosterols are cholesterol and some steroid hormones; the most important phytosterols are campesterol, sitosterol and stigmasterol. Sterols play essential roles in the physiology of eukaryotic organisms. For example cholesterol forms part of the cellular membrane where its presence affects the cell membrane's fluidity and serves as secondary messenger in developmental signaling. Plant sterols are also known to block cholesterol absorption sites in the human intestine thus helping to reduce cholesterol in humans. In humans, sterols act to provide important signals and metabolic communications eg. circadian rhythms, blood clotting.

In a preferred embodiment the sterol is cholesterol, a cholesterol derivative, 7-dehydro-cholesterol, lanosterol, a lanosterol derivative, zymosterol, a zymosterol derivative, lathosterol, a lathosterol derivative, cucurbitacin, a cucurbatin derivative, episterol, a episterol derivative, teasterone, a teasterone derivative, castasterone, a castasterone derivative, typhasterol, a typhasterol derivative, cathasterone, a cathasterone derivative, cycloeucalenol, a cycloeucalenol derivative, sitosterol, a sitosterol derivative, isofucosterol, a isofucosterol derivative, fucosterol, a fucosterol derivative, gorgosterol, a gorgosterol derivative, ergosterol, an ergosterol derivative, stigmasterol or a stigmasterol derivative.

In particular, in an organism, wherein an acylester of 7-dehydro-cholesterol is accumulated, the activities of HMG-CoA-reductase (EC1.1.1.34), and/or Δ24-reductase, and/or lanosterol C14-demethylase/cytochrome P450 51 (EC 1.14.13.70), and/or squalene-epoxidase/squalene-monoxygenase (EC 1.14.99.7) may increased in comparison with a corresponding wildtype organism. Additionally, the activities of SAM:C-24 sterol methyl transferase, and/or C-22 sterol desaturase and/or C-5 sterol desaturase may be reduced or abolished in comparison with a corresponding wildtype organism. In an organism, wherein an acylester of ergosterol is accumulated, the activities of HMG-CoA-reductase (EC1.1.1.34), and/or lanosterol C14-demethylase/cytochrome P450 51 (EC 1.14.13.70) and/or squalene-epoxidase/squalene-monoxygenase (EC 1.14.99.7), may be increased in comparison with a corresponding wildtype organism. In an organism, wherein an acylester of episterol is accumulated, the activities of HMG-CoA-reductase (EC1.1.1.34), and/or lanosterol C14-demethylase/cytochrome P450 51 (EC 1.14.13.70), and/or squalene-epoxidase/squalene-monoxygenase (EC 1.14.99.7) may be increased in comparison with a corresponding wildtype organism and/or Δ22-desaturase/cytochrome P450 61 (EC 1.14.14.1) activity may reduced in comparison with a corresponding wildtype organism.

In another preferred embodiment the steroid is androsterone, an androsterone derivative, testosterone, a testosterone derivative, androstenediol, an androstenediol derivative, androstenedione, an androstenedione derivative, calusterone, a calusterone derivative, methandriol, a methandriol derivative, bolasterone, a bolasterone derivative, epiandrosterone, an epiandrosterone derivative, mestanolone, a mestanolone derivative, stanolone, a stanolone derivative, stenbolone, a sten bolone derivative, epitestosterone, an epitestosterone derivative, cortisol, a cortisol derivative, aldosterone, an aldosterone derivative, pregnenolone, a pregnenolone derivative, cortisone, a cortisone derivative, corticosterone, a corticosterone derivative, norethindrone, a norethindrone derivative, urocortisol or an urocortisol derivative.

In a preferred embodiment of the fifth and sixth aspect of the present invention the organism which is capable of accumulating an acyl ester of a sterol lipid is an organism which naturally possesses the biosynthetic pathway leading to the synthesis of the respective sterol lipid and in which, more preferably, enzymatic activities of the corresponding pathway are increased in comparison to a corresponding non-modified organism in order to obtain a higher accumulation of the respective sterol lipid.

In a preferred embodiment, the organism according to aspects 1 to 6 of the invention is capable of accumulating in its lipid particle a prenol lipid. Prenol lipids are synthesized from the 5-carbon precursors isopentenyl diphosphate and dimethylallyl diphosphate that are produced mainly via the mevalonic acid (MVA) pathway. The prenol lipids encompass isoprenoids, quinones and hydroquinones, polyprenols, hopanoids and some other minor types. The simple isoprenoids (linear alcohols, diphosphates, etc.) are formed by the successive addition of C5 units, and are classified according to number of these terpene units. Structures containing greater than 40 carbons are known as polyterpenes. Carotenoids are important simple isoprenoids that function as anti-oxidants and as precursors of vitamin A. Another biologically important class of molecules is exemplified by the quinones and hydroquinones, which contain an isoprenoid tail attached to a quinonoid core of non-isoprenoid origin. Vitamin E and vitamin K, as well as the ubiquinones, are examples of this class. Bacteria synthesize polyprenols (called bactoprenols) in which the terminal isoprenoid unit attached to oxygen remains unsaturated, whereas in animal polyprenols (dolichols) the terminal isoprenoid is reduced.

In a preferred embodiment the prenol lipid accumulated in the lipid particles is an isoprenoid. The isoprenoids include e.g. C5 isoprenoids, C10 isoprenoids (monoterpenes), C15 isoprenoids (sequiterpenes), C20 isoprenoids (diterpenes), C25 isoprenoids (sesterterpenes), C30 isoprenoids (triterpenes), C40 isoprenoids (tetraterpenes), polyterpenes and retinoids.

In a particularly preferred embodiment, the isoprenoid is a triterpene. Triterpenes consist of six isoprene units and have the basic molecular formula $C_{30}H_{48-50}$. This group encompasses, e.g. 3S-squalene-2,3-epoxide, squalene, presqualene diphosphate, tetrahymanol, α-amyrin, β-amyrin, lupeol, lupeol acetate, taraxasterol, azadirachtin A, neoquassin, quassin and 3-acetyl-1-tigloylazadirachtinin. The linear triterpene squalene, the major constituent of shark liver oil, is derived from the reductive coupling of two molecules of farnesyl pyrophosphate. Squalene is then processed biosynthetically to generate either lanosterol or cycloartenol, the structural precursors to all the steroids.

In an especially preferred embodiment the prenol lipid accumulated in the lipid particles is squalene or a squalene derivative. A squalene derivative comprises one or more, in particular 1 to 10 or 1 to 4, additional methyl or ethyl groups bound to backbone carbon atoms instead of hydrogen atom(s) bound to backbone carbon atoms in squalen.

In a particularly preferred embodiment the organism according to the invention, preferably in connection with the first, third and fifth aspect of the invention, is an organism which does not produce and store in its lipid particles wax esters, e.g. a fungal organism as described above, and more preferably a fungal organism of the genus *Saccharomyces*, most preferably *Saccharomyces cerevisiae*. Such an organism which is, according to the first, third and fifth aspect of the invention, modified so as to not synthesize a triacylglycerol and/or a steryl acyl ester, is capable of synthesizing and storing in its lipid particles prenol lipids, in particular squalene, thereby allowing the production of such a prenol lipid in the lipid particles in basically pure or purer form. Thus, already by eliminating in a yeast organism the synthetic pathways for the biosynthesis of TAGs and/or SAEs is it possible to dramatically improve the production concerning the amount and purity of the squalene produced by such an organism.

A further improvement in squalene production in such an organism could be achieved by modifying the organism's metabolism so as to increase the enzyme activities leading to the synthesis of squalene and reducing enzyme activities of pathways which convert squalene into other compounds.

The genes of the squalene biosynthetic pathway are known and cloned, e.g., in the yeast *S. cerevisiae*. The major bottleneck enzyme is the HMG-CoA-reductase (HMG1) (Basson et al. (Mol. Cell. Biol. 8 (1988), 3793-3808). Thus, in a preferred embodiment the organism according to the first, third or fifth aspect of the present invention is capable of accumulating squalene in lipid particles and is characterized in that the activity of HMG-CoA-reductase (EC1.1.1.34) is increased in comparison with a corresponding non-modified organism, preferably with a corresponding wildtype organism. The increase in HMG-CoA-reductase activity can be achieved by means and methods well known to the person skilled in the art which are also described in more detail further below. In a preferred embodiment the increase in activity of HMG-CoA-reductase is achieved by expressing in the organism a HMG-CoA-reductase gene which codes only for the catalytic area of the enzyme but does not code for the membrane-bound domains. Such an alteration is already described in EP-A 486 290. By this modification feedback regulation of the HMG-CoA-reductase by intermediates of the ergosterol biosynthesis pathway is avoided. In another preferred embodiment, the gene encoding HMG-CoA-reductase in the organism according to the invention is placed under the control of a heterologous promoter, i.e. a promoter which is foreign to the HMG-CoA-reductase gene, in particular this promoter is a promoter which is not regulated in its activity by intermediates of the ergosterol biosynthesis pathway. An example of a suitable promoter is the ADH1 promoter, in particular the "average" ADH1 promoter which shows an approximately constitutive expression (Ruohonen et al., Journal of Biotechnology 39 (1995), 193-203).

In some organisms, such as yeast, squalene can be converted into other compounds, in particular into ergosterol and into intermediates of the ergosterol biosynthesis pathway. The chemical reactions and pathways resulting in the formation of the sterol ergosterol ((22E)-ergosta-5,7,22-trien-3-beta-ol) occur in ergot, yeast and moulds. In these organisms squalene is converted by squalene monooxygenase/squalene epoxidase (EC 1.14.99.7; also referred to as squalene epoxidase or ERG1) into (S)-2,3-epoxysqualene which is subsequently converted by 2,3-oxidosqualene-lanosterol cyclise (EC 5.4.99.7; ERG7) into lanosterol. Lanosterol is then converted by cytochrome P450 lanosterol 14a-demethylase (EC 1.14.13.70; ERG11) using NADPH and $O_2$ into 4,4-dimethyl-cholesta-8,14,24-trienol which is then converted by C14 sterol reductase (EC 1.3.1.70; ERG24) using NADPH into 4,4-dimethyl-8,24-cholestadienol. This compound is then further converted by the action of C-4 sterol methyl oxidase (EC 1.14.13.72; ERG25) into 4-methyl-8,24-cholestadienol. This substance is converted by C-3 sterol dehydrogenase (EC 1.1.1.170; ERG26) into 3-keto-4-methylzymosterol. Subsequently 3-keto-4-methylzymosterol is converted by 3-keto sterol reductase (EC 1.1.1.270; ERG27) into zymosterol. Zymosterol itself is then together with S-adenosyl-L-methionine converted by the action of SAM:C-24 sterol methyltransferase (EC 2.1.1.41; ERG6) into fecosterol and S-adenosyl-homocystein. Fecosterol is then converted by the action of C-8 sterol isomerase (ERG2) into episterol which is then converted by the action of C-5 sterol desaturase (EC 1.14.21.6; ERG3) by using NADPH and $O_2$ into 5,7,24(28)-ergostatrienol. This compound is further converted by the action of C-22 sterol desaturase (EC 1.14.14; ERG5) into 5,7,22,24(28)-ergostatetraenol. 5,7,22,24(28)-ergostatetraenol is then converted by the action of C-24 sterol reductase (EC 1.3.1.71; ERG4) into ergosterol. If it is desired that the organism according to the invention accumulates squalene in the lipid particles and if this organism is derived from an organism which is naturally capable of synthesizing ergosterol or intermediates of the ergosterol pathway starting from squalene, it may be desirable to reduce the activities of one or more of the above mentioned enzyme activities of the pathway leading from squalene to ergosterol in the organism. In principle, any one, more than one or all of the above mentioned enzymes of the above described ergosterol pathway could be reduced. In a preferred embodiment, the activity of squalene monooxygenase (EC 1.14.99.7; also referred to as squalene epoxidase or ERG1) is reduced, however, not completely eliminated since some sterol synthesis is necessary for the viability of the yeast cells. It is also possible to reduce the activity of one or more of the following enzymes involved in the biosynthesis of ergosterol: SAM:C-24 sterol methyl transferase (EC 2.1.1.41), C-22 sterol desaturase (EC 1.14.14) and C-5 sterol desaturase (EC 1.14.21.6). All this applies to any of the aforementioned embodiments of the invention.

As part of the invention, but of independent nature the following features with respect to genetically modified organisms apply.

Within the invention it has also been found that the constitutive overexpression of the genes SAK1 and/or HAP4 in the yeast Saccharomyces cerevisiae leads to a highly increased productivity of lipids in particular of squalene and sterols. The genes SAK1 and HAP4 are related to the respiro-fermentative flux distribution.

The gene SAK1 encodes for an upstream serine/threonine kinase responsible for the phosphorylation of the Snf1p/Snf4p complex. The phosphorylation leads to an active Snf1p/Snf4p complex which is localized in the nucleus. The Snf1p/Snf4p complex belongs to the protein serin/threonin kinases and plays a central role in the relief of the glucose-repression during the "diauxic shift". The diauxic shift denotes the shift from the fermentative to the respirative metabolism when glucose or other fermentative carbon sources in the medium are consumed. The Snf1/Snf4 complex ranges far up in the hierarchy of the cascade responsible for the glucose-repression and derepression, respectively. In the course of the diauxic shift the expression level of about a quarter of the 6000 genes of Saccharomyces cerevisiae is changed significantly. These major changes mainly address the central metabolism which is shifted from the fermentative mode to the respiratory mode. In the fermentative mode the yeast cell metabolizes fermentable carbon sources like glucose to ethanol and carbondioxide. In the respiratory mode the produced ethanol is respired to gain adenosintriphosphate (ATP), which provides energy in the cell. In the course of the diauxic shift the Snf1p/Snf4p complex is phosphorylated and therefore activated by the Snf1-kinases Sak1p, Tos1p und Elm1p. The activated complex is localized in the nucleus where it influences the two transcription factors Mig1p und Cat8p. The zinc finger protein Mig1p is a transcriptional repressor, which recruits the proteins Tup1p and Cyc8p to bind a certain consensus sequence of a large number of glucose repressed genes as a complex whereby the transcription of the gene downstream of this consensus sequence is repressed. Cat8p is a transcriptional activator and induces the expression of at least 34 genes, when glucose in the medium is exhausted. These genes are mainly genes of the glyoxylate shunt, which is necessary for the metabolization of C2 compounds like ethanol or acetate. In addition to that also genes responsible for the intracellular transport of intermediates of the citric acid cycle and the glyoxylate shunt are regulated by Cat8p. The active Snf1p/Snf4p complex phosphorylates Mig1p, whereby this protein is inactivated and translocated out of the nucleus and phosphorylates Cat8p and Sip1p, a functional homologue, which leads to an inactivation of these two proteins. An active Snf1p/Snf4p complex localized in the nucleus therefore considerably contributes to the relief of the glucose repression and the shift from fermentation to respiration, because it influences several transcription factors of the repression cascade. Accordingly, an organism according to the present invention may be further developed so that it exhibits a more active Snf1p/Snf4p complex even in the presence of glucose. This modification is achieved by the transcriptional deregulation of the protein Sak1p, which is responsible as the main kinase for the phosphorylation and therefore the activation of the Snf1p/Snf4p complex.

The Hap2/3/4/5 protein complex regulates a large number of glucose-repressed genes. These are predominantly genes of the respiration chain and the citric acid cycle. As an activator it induces the transcription of these genes during the diauxic shift and strongly contributes to a shift of the respiro-fermentative balance in the direction of respiration. The genes HAP2, HAP3 and HAP5 are expressed constitutively. Naturally HAP4 is only expressed during growth on non-fermentable carbon sources. During a cultivation of a HAP4-overexpression mutant strain it was observed that this mutation leads to an increased growth rate, biomass- and acetate production and to a reduced formation of glycerol and ethanol. The Hap2/3/4/5 protein complex propagates the respiratory system by increasing the respiratory capacity, the mitochondrial biogenesis and the carbon flux through the citric acid cycle.

Another observation within the invention is that the deletion of the gene FLD1 leads to an unexpected significant increase of the lipid production, in particular of the squalene production, in organisms like yeasts, in particular the yeast *Saccharomyces cerevisiae*. The gene FLD1 encodes for a seipin protein involved in lipid droplet morphology, number and size. It was reported that an overexpression of FLD1 leads to the fusion of lipid particles which results in the formation of significantly enlarged, but fewer lipid particles in the yeast cell. In a wildtype yeast strain squalene is an intermediate in the sterol biosynthetic pathway and does not accumulate in the cell. An increased activity of the HMG-CoA-reductase, which is achieved by expressing in the yeast a HMG-CoA-reductase gene, which codes only for the catalytic part of the enzyme, but does not code for the membrane-bound domains as described in EP-A 486 290, leads to an accumulation of squalene in the cell. This accumulation is due to an avoidance of feedback regulation of the HMG-CoA-reductase by intermediates of the ergosterol biosynthesis pathway. Within the framework of this invention it was observed that the deletion of the gene FLD1 leads to an unexpected significant increase of the lipid production in particular of the squalene production in yeast strains exhibiting an increased HMG-CoA-reductase activity.

The above findings with respect to SAK1, HAP4 and FLD1 lead to further improvements and embodiments within any of the six aspects of the invention, as described above. However, these findings are also of independent value for organisms, which do not comprise the modifications described above, but have the ability to synthesize all lipids typically synthesized by the respective unmodified organisms. Unmodified organisms in this context comprise aside the wild type such organisms, which have an increased HMG-CoA-reductase (EC1.1.1.34) activity, compared with the corresponding wild type organism.

Accordingly, the present invention also comprises an isolated genetically modified non-mammalian organism, wherein the genes HAP4 and/or SAK1 are transcriptionally deregulated and/or overexpressed and/or wherein the gene FLD1 is repressed or inactivated or deleted, all in comparison with a corresponding wildtype organism. Specifically, one of the genes HAP4 and SAK1, or both, can be put under the control of a constitutively active promoter, like a (optionally) ADH1 promoter. In a further embodiment of this variant the gene REG1 is repressed or inactivated or deleted, in comparison with a corresponding wildtype organism. Aside this, all previous comments with respect to the invention apply to this independent aspect in an analogous manner and any of the features disclosed previously can be incorporated in this independent aspect as well.

The present invention also relates to a method for producing the second lipid, wherein an organism of the invention is used and cultured, and wherein the second lipid is isolated from the organism. For example, a method of the invention for producing a prenol lipid comprises culturing the organism of the third or fourth aspect of the invention as described above, which is capable of accumulating in its lipid particles a prenol lipid. With respect to the prenol lipid to be accumulated, the same applies for the preferred embodiments as has been described above in connection with the organism of the third and fourth aspect of the present invention. The same holds true for the enzyme activities which are reduced or increased in a corresponding organism. As another example, a method for producing a steryl acyl ester comprises the culturing of an organism according to the fifth or sixth aspect of the present invention.

The reduction in activity of an protein or enzyme as mentioned hereinabove in comparison to a corresponding non-modified organism is preferably at least 50%, more preferably at least 75%, even more preferably at least 80%, particularly preferred at least 90% and most preferred 100%. A reduction of 100% means that there is no protein or enzyme activity of said enzyme present in said organism. The increase in activity of an enzyme or protein as mentioned hereinabove in comparison to a corresponding non-modified organism is preferably at least 10%, more preferably at least 50%, even more preferably at least 200%, particularly preferred at least 1000%. The phrase "increase" also comprises presence of (any measurable) enzymatic activity of an enzyme or protein in case that the non-modified organism does not comprise any measurable such activity. The phrase "increase in activity" further encompasses an increase in the amount of a protein in all those cases, wherein the protein is no enzyme (like HAP4). Then the above parameters of increase apply in an analogous manner to the amounts. The activities of enzymes can be measured by adding to a predetermined amount of an educt a predetermined amount of an enzyme, which catalyzes the reaction of the educt to a product, and optionally additionally required reaction components, and by measuring the amount of product synthesized within a predetermined period of time. Specific methods for the measurement of activities of enzyme discussed above are disclosed e.g. in the document WO 03/064650 A1. The measurement of activities of above-mentioned enzymes not described in said document is performed in analogous manner.

Methods for reducing the activity of a given enzyme in a cell are, for example, reducing or abolishing the gene expression of the gene coding for the enzyme, e.g. by implementing a weaker promoter upstream of the corresponding gene or by complete or partial deletion of the gene and/or the related promoter, and/or adding an enzyme inhibitor to inhibit the translated enzyme within a cell of the organism and/or incorporation of si RNA into the cells to reduce the amount of active transcript and/or mutation of the gene to generate a less active variant.

A reduction in gene expression means that the level of gene expression of a nucleotide sequence encoding the respective enzyme is reduced in comparison to the level of gene expression of said nucleotide sequence in a corresponding non-modified organism, preferably a corresponding wildtype organism. The same levels of reduction as provided above with respect to activities apply. Means and methods for detecting the level of gene expression include, e.g., the determination of the amount of synthesized corresponding mRNA or protein or the determination of the enzymatic activity of the respective protein. In a preferred embodiment the level of gene expression is determined by measuring the amount of mRNA, e.g. in Northern Blot. In another preferred embodiment the level of gene expression is determined by measuring the amount of synthesized corresponding protein, e.g. in a Western Blot, or by determining the amount of the corresponding enzymatic activity. The reduction in gene expression may also be achieved by rendering the gene in question non-functional. One possible means for rendering a gene non-functional is gene disruption.

Methods for increasing the activity of an enzyme include transformation of cells such that a transcriptional deregulation is achieved, such that a gene (heterologous or homologous) coding for the enzyme is arranged under the control of a constitutively active (homologous or heterologous) promoter, and/or such that the number of copies of the (heterologous or homologous) gene coding for the enzyme is increased and/or increasing the activity by mutation.

Specific examples for effecting increased or decreased enzymatic activities are provided in the examples. The skilled artisan will, however, also be able to apply other methods well known in the art without needing specific disclosure herein.

Suitable gene sequences for enzymes employed in the instant invention are disclosed in the following, but other gene sequences having the same enzymatic activities may be employed just as well. Not the particular gene sequences or the protein sequences coded thereby are relevant structural features within the instant invention, but instead the classification under the same EC (Enzyme Commision) numbers.

Gene sequences for acyl-CoA:sterol acyltransferase/sterol O-acyltransferase (EC 2.3.1.26) include: NC_001135.4, NC_001147.6, NM_005891, NM_144784, NM_153728.

Gene sequences for diacylglycerol acyltransferase/diacylglycerol O-acyltranferase (EC 2.3.1.20) include: NC_001147.5, XM_002478787, NM_123089, XM_002378082, NM_032564, NM_001012345, NM_010046, XM_002146497.

Gene Sequences for lecithin cholesterol acyl transferase/phospholipid:diacylglycerol acyltransferase (EC 2.3.1.158) include: NC_001147.6, NM_008490, NM_001162568, NM_000229, NM_001005715, NM_017024, NM_001082190.

Gene sequences for acyl CoA-wax alcohol acyltransferase (EC 2.3.1.75) include: NM_123089, NM_177448.

Gene sequences for HMG-CoOA-reductases include: NC_001145, NM_106299, NC_003421.2, NC_009784.1, NC_003028.3, NC_007308.3, and the sequence of FIG. 5 (truncated, tHMG1).

Gene sequences for C-24 sterol methyl transferases include: NC_001145, NC_000911.1, NC_003423.3, XM_505173, XM_716615.

Gene sequences for C-22 sterol desaturases include: NC_003424.3, NC_009046.1, NC_001145.2, XM_500188, XM_711840.

Gene sequences for C-5 sterol desaturases include: NC_001144, S46162, NG_009446, NM_053642, NM_001035356, XM_503090, XM_708519.

Gene sequences for HAP4 include: NC_001143.7, XM_448596, XM_001645329.

Gene sequences for SAK1 include: NC_001137.2, XM_502591, XM_448319, XM_453478, NM_208704.

Gene Sequences for REG1 include: NC_001136.8, XM_500990, XM_448729, XM_455276.

Gene sequences for FLD1 include: NC_001144.4, NM_210286, XM_001647166, XM_449778.

Gene sequences for 7-dehydrocholesterol reductase include: NM_103926, NM_001360, NM_007856, NM_203904, NM_001014927, NM_201330, NM_022389, NM_001131727, NM_001087087, XM_001497598, XM_001174160, XM_001099101, BM490402, CA753545.

Gene sequences for 24-dehydrocholesterol reductase include: NM_014762, NM_001016800, NM_001094456, NM_001008645, NM_001103276, NM_001080148, NM_053272, NM_00103128, XM_001488247, AB125202, XM_001153751.

Gene sequences for lanosterol sterol 14-demethylases include: NC_001140.5, XM_500518, EF059165, XM_445876, XM_454109.

Gene sequences for squalene monooxygenases include: NC_001139.8, M64994, XM_503994, XM_706801, XM_455763

Gene sequences for suitable promoters (promoters of the respective different enzymes expressed heterologously may be the same or different) include: NC_001142, NC_001139, NC_001147, NC_001139, NC_001148, NC_001135, NC_001136.

Generally the organism according to the present invention (regardless of which of the aspects described above) can be any possible non-human, preferably non-mammalian organism. Examples for suitable organisms are provided in the claims.

FIG. 1 Thin layer chromatography of whole lipid extracts from constructed mutant strains of the yeast *Saccharomyces cerevisiae*

FIG. 5 shows the sequence of a truncated HMG CoA-reductase, tHMG1.

Figure 1:
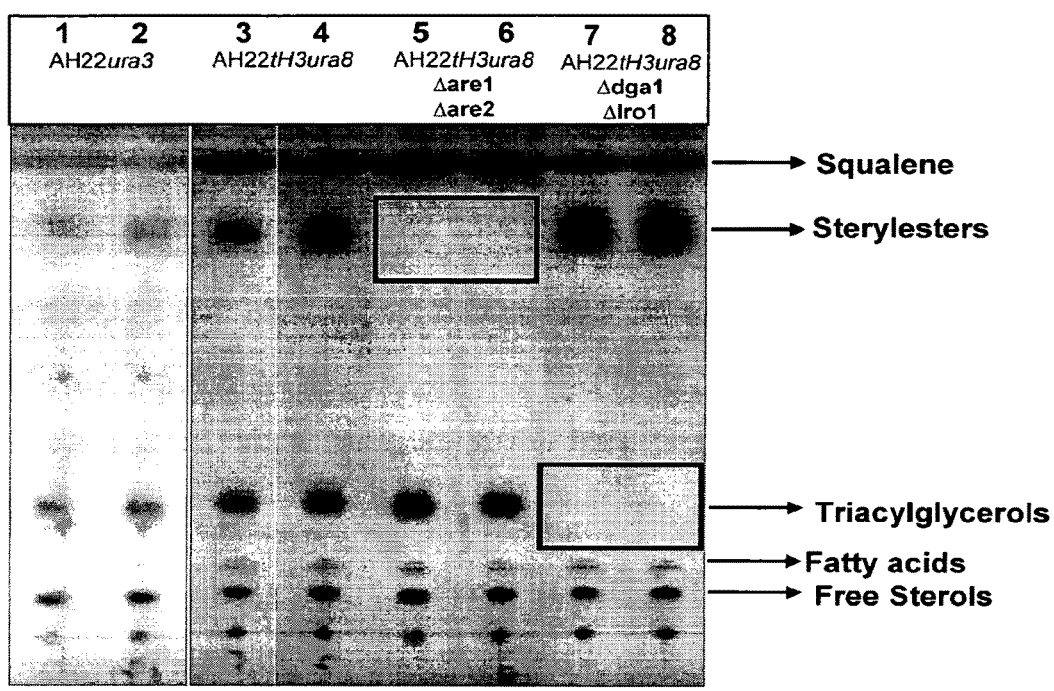
Figure 2:
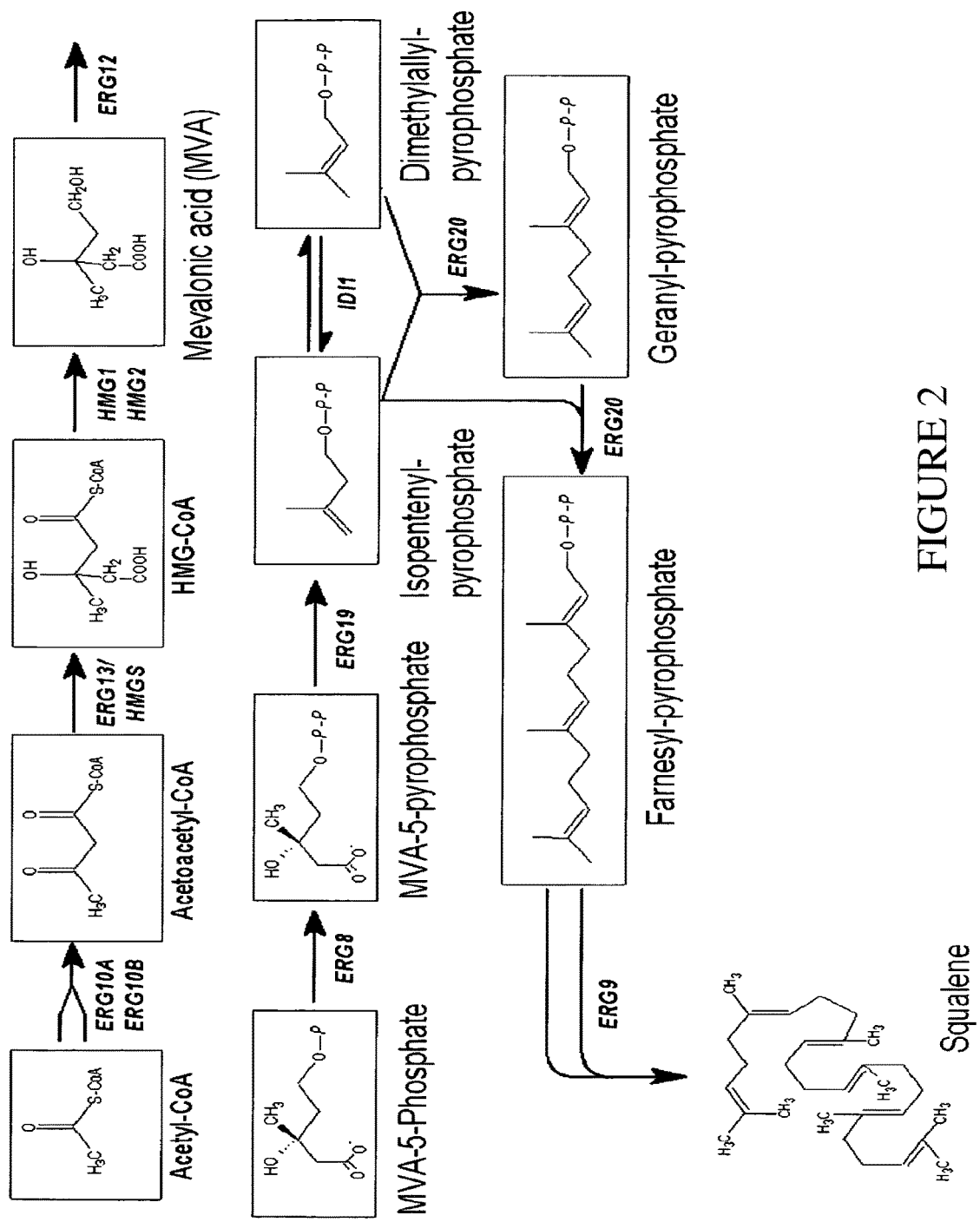
FIG. 2 shows schematically the biosynthesis of squalene in the yeast *Saccharomyces cerevisiae*.
Figure 3:
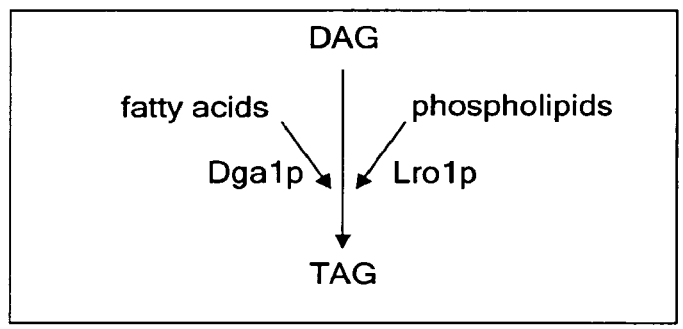
FIG. 3 shows schematically the biosynthesis of triacylglyceroles in the yeast *Saccharomyces cerevisiae*.
Figure 4:
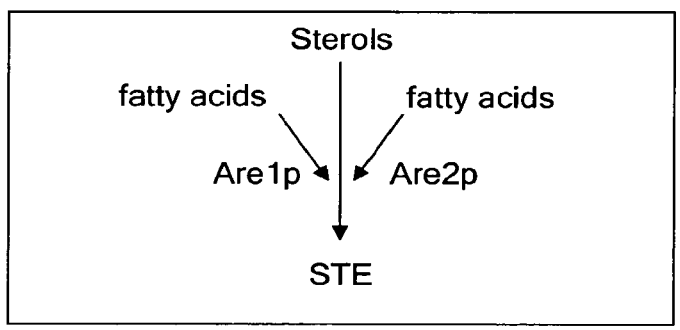
FIG. 4 shows schematically the biosynthesis of steryl acyl ester in the yeast *Saccharomyces cerevisiae*.

The following Examples serve merely to illustrate the invention.

The following materials and methods have been used in the examples.

1. Restriction Cleavages

The restriction of plasmids (1 to 10 μg) was performed in 30 μl batches. To this end, the DNA was taken up in 24 μl of H$_2$O, and mixed with 3 μl of the corresponding buffer, 1 μl of RSA (bovine serum albumin) and 2 μl of enzyme. The enzyme concentration was 1 unit/μl or 5 units/μl depending on the amount of DNA. In some cases, 1 μl more of RNase was added to the batch to degrade the tRNA. The restriction batch was incubated for two hours at 37° C. The restriction was controlled with a minigel.

2. Gel Electrophoreses

The gel electrophoreses were performed in minigel or wide-minigel equipment. The minigels (about 20 ml, 8 bags) and the wide-minigels (50 ml, 15 or 30 bags) consisted of 1% agarose in TAE. 1*TAE was used as a mobile buffer. The samples (10 μl) were mixed with 3 μl of stopper solution and applied. I-DNA cut with HindIII was used as a standard (bands at: 23.1 kb; 9.4 kb; 6.6 kb; 4.4 kb; 2.3 kb; 2.0 kb; 0.6 kb). For separation, a voltage of 80 V for 45 to 60 minutes was prepared. Then, the gel was stained in ethidium bromide solution and held under UV light with video-documentation system INTAS or photographed with an orange filter.

3. Gel Elution

The desired fragments were isolated using gel elution. The restriction preparation was applied in several bags of a minigel and separated. Only [lambda]-HindIII and a "sacrifice trace" were stained in ethidium bromide solution, viewed under UV light, and the desired fragment was labeled. As a result, DNA was prevented from damaging the residual bags by the ethidium bromide and the UV light. By aligning the stained and unstained gel pieces, the desired fragment from the unstained gel piece could be cut out based on the labeling. The agarose piece with the fragment to be isolated was added in a dialysis tube, sealed free of air bubbles with a little TAE buffer and placed in the BioRad-minigel apparatus. The mobile buffer consisted of 1*TAE, and the voltage was 100 V for 40 minutes. Then, the flow polarity was varied for 2 minutes to loosen the DNA adhering to the dialysis tube. The buffer that contains the DNA fragments of the dialysis tube was moved into the reaction vessel and thus performed an ethanol precipitation. To this end, fraction (1/10) volume of 3 M sodium acetate, tRNA (1 µl per 50 µl of solution) and 2.5 times the volume of ice-cold 96% ethanol were added to the DNA solution. The batch was incubated for 30 minutes at −20° C. and then centrifuged off at 12,000 rpm for 30 minutes at 4° C. The DNA pellet was dried and taken up in 10 to 50 µl of $H_2O$ (depending on the amount of DNA).

4. Klenow Treatment

Projecting ends of DNA fragments are made up by the Klenow treatment, so that "blunt ends" result. Per 1 µg of DNA, the following batch was pipetted together: In this case, the DNA should be derived from an ethanol precipitation to prevent contaminants from inhibiting the Klenow-polymerase. Incubation was carried out for 30 minutes at 37° C., and then over another 5 minutes at 70° C. the reaction was halted. The DNA was obtained from the batch by an ethanol precipitation and taken up in 10 µl of $H_2O$.

5. Ligation

The DNA fragments that were to be ligated were combined. The end volume of 13.1 µl contained about 0.5 µg of DNA with a vector-insert ratio of 1:5. The sample was incubated for 45 seconds at 70° C., cooled to room temperature (about 3 minutes) and then incubated on ice for 10 minutes. Then, the ligation buffers were added: 2.6 µl of 500 mmol TrisHCl, pH 7.5, and 1.3 µl of 100 mmol $MgCl_2$, and they were incubated on ice for another 10 minutes. After 1 µl of 500 mmol DTT and 1 µl of 10 mmol ATP were added, 1 µl of ligase (1 unit/µl) was added on ice for another 10 minutes. The entire treatment should be carried out with as little shaking as possible so as to keep adjacent DNA ends from reseparating, The ligation was carried out overnight at 14° C.

6. E. coli Transformation

Component *Escherichia coli* (*E. coli*) NM522 cells were transformed with the DNA of the ligation preparation. As a positive control, a batch was supplied with 50 ng of the pScL3 plasmid, and as a null control, a batch was supplied without DNA. For each transformation preparation, 100 µl of 8% PEG solution, 10 µl of DNA and 200 µl of competent cells (*E. coli* NM522) were pipetted into a tabletop centrifuging tube. The batches were put on ice for 30 minutes and shaken intermittently. Then, thermal shock took place: 1 minute at 42° C. For regeneration, 1 ml of LB-medium was added to the cells and incubated on a shaker for 90 minutes at 37° C. 100 µl each of the undiluted batches, a 1:10 dilution and a 1:100 dilution were flattened out on LB+ampicillin plates and incubated overnight at 37° C.

7. Plasmid Isolation from E. coli (Miniprep)

*E. coli* colonies were cultured overnight in 1.5 ml of LB+ampicillin medium in tabletop centrifuging tubes at 37° C. and 120 rpm. The next day, the cells were centrifuged off for 5 minutes at 5000 rpm and 4° C., and the pellet was taken up in 50 µl of TE-buffer. Each batch was mixed with 100 µl of 0.2N NaoH, 1% SDS solution, mixed and put on ice for 5 minutes (lysis of the cells). Then, 400 µl of Na-acetate/Nacl solution (230 µl of $H_2O$, 130 µl of 3 M sodium acetate, and 40 µl of 5 M NaCl) was added, the batch was mixed and put on ice for another 15 minutes (protein precipitation). After 15 minutes of centrifuging at 11,000 rpm, the supernatant, which contains plasmid-DNA, was transferred into an Eppendorf vessel. If the supernatant was not completely clear, it was centrifuged one more time. The supernatant was mixed with 360 µl of ice-cooled isopropanol and incubated for 30 minutes at −20° C. (DNA precipitation). The DNA was centrifuged off (15 minutes, 12,000 rpm, 4° C.), the supernatant was discarded, the pellet was washed in 100 µl of ice-cooled 96% ethanol, incubated for 15 minutes at −20° C. and centrifuged off again (15 minutes, 12,000 rpm, 4° C.). The pellet was dried in a speed vacuum and then taken up in 100 µl of $H_2O$. The plasmid-DNA was characterized by restriction analysis. To this end, 10 µl of each batch was restricted and cleaved by gel electrophoresis in a wide-minigel (see above).

8. Plasmid-Isolation on E. coli (Maxiprep)

To isolate larger amounts of plasmid-DNA, the maxiprep method was performed. Two plungers with 100 ml of LB+ampicillin medium were inoculated with a colony or with 100 µl of a frozen culture, which carries the plasmid that is to be isolated, and it was incubated overnight at 37° C. and 120 rpm. The next day the culture (200 ml) was moved into a GSA beaker and centrifuged for 10 minutes at 4000 rpm (2600*g). The cell pellet was resuspended in 6 ml of TE-buffer. To digest the cell wall, 1.2 ml of lysozyme solution (20 mg/ml of TE-buffer) was added, and it was incubated for 10 minutes at room temperature. Then, the lysis of the cells was carried out with 12 ml of 0.2N NaOH, 1% SDS solution and for another 5 minutes of incubation at room temperature. The proteins were precipitated by the addition of 9 ml of cooled 3 M sodium acetate solution (pH 4.8) and a 15-minute incubation on ice. After centrifuging (GSA: 13,000 rpm (27.500*g), 20 minutes, 4° C.), the supernatant, which contained the DNA, was moved into a new GSA beaker, and the DNA was precipitated with 15 ml of ice-cold isopropanol and an incubation of 30 minutes at −20° C. The DNA pellet was washed in 5 ml of ice-cooled ethanol and dried in air (about 30-60 minutes). Then, it was resuspended in 1 ml of $H_2O$. An examination of the plasmid by restriction analysis took place. The concentration was determined by depositing dilutions on a minigel. To reduce the salt content, a 30-60 minute microdialysis was carried out (pore size 0.025 µm).

9. Yeast Transformation

For the yeast transformation, a pre-culture of the strain *Saccharomyces cerevisiae* (*S. cerevisiae*) AH22 was prepared. A plunger with 20 ml of YE-medium was inoculated with 100 µl of the frozen culture and incubated overnight at 28° C. and 120 rpm. The main cultivation was carried out under identical conditions in a plunger with 100 ml of YE-medium, which was inoculated with 10 µl, 20 µl or 50 µl of the pre-culture.

9.1 Producing Competent Cells

The next day, the plungers were counted out using a Thoma chamber, and the procedure was continued with the plunger, which held $3-5*10^7$ cells/ml. The cells were harvested by centrifuging (GSA: 5000 rpm (4000*g), 10 minutes). The cell pellet was resuspended in 10 ml of TE-buffer and divided into two tabletop centrifuging tubes (5 ml each). The cells were centrifuged off for 3 minutes at 6000 rpm and washed twice with 5 ml of TE-buffer each. Then, the cell pellet was taken up in 330 µl of lithium acetate buffer per $10^9$ cells, transferred into a sterile 50 ml Erlenmeyer flask and shaken for one hour at 28° C. As a result, the cells were competent for transformation.

9.2 Transformation

For each transformation preparation, 15 µl of herring sperm DNA (10 mg/ml), 10 µl of DNA that is to be transformed (about 0.5 µg) and 330 µl of component cells were pipetted into a tabletop centrifuging tube and incubated for 30 minutes at 28° C. (without shaking!). Then, 700 µl of 50% PEG 6000 was added, and it was incubated for one additional hour at 28° C., without shaking. A thermal shock of 5 minutes at 42° C. followed. 100 µl of the suspension was plated on selective medium (YNB, Difco) to select for leucine prototrophy. In the case of the selection on G418 resistance, a regeneration of the cells is carried out after the thermal shock (see under 9.3 Regeneration Phase).

9.3 Regeneration Phase

Since the selection marker is resistance to G418, the cells needed time for the expression of the resistance-gene. The transformation preparations were mixed with 4 ml of YE-medium and incubated overnight at 28° C. in the shaker (120 rpm). The next day, the cells were centrifuged off (6,000 rpm, 3 minutes), taken up in 1 ml of YE-medium, and 100 µl or 200 µl was flattened out on YE+G418 plates. The plates were incubated for several days at 28° C.

10. Reaction Conditions for the PCR

The reaction conditions for the polymerase chain reaction must be optimized for the individual case and are not necessarily valid for any batch. Thus, i.a., the amount of DNA used, the salt concentrations and the melting temperature can be varied. For our formulation of the problem, it has proven advantageous to combine the following substances in an Eppendorf cap, which was suitable for use in a thermocycler: 5 µl of super buffer, 8 µl of dNTP's (0.625 µM each), 5'-primer, 3'-primer and 0.2 µg of matrix DNA, dissolved in enough water to yield a total volume of 50 µl for the PCR preparation, were added to 2 µl (~0.1 U) of Super Taq polymerase. The batch was briefly centrifuged off and covered with a drop of oil. Between 37 and 40 cycles were selected for amplification.

11. Isolation of Lipid Particles from *S. cerevisiae*

Yeast cells were grown in 50 ml of WMVIII minimal medium for 72 h at 28° C. with reciprocal shaking at 250 rpm. Cells were harvested by centrifugation and lipid particles were isolated and purified according to Leber et al. (Leber R, Zinser E, Zellnig G, Paltauf F, Daum G. Characterization of lipid particles of the yeast, *Saccharomyces cerevisiae*. Yeast. 1994 November; 10(11):1421-1428). For sterol analysis lipid particles were either saponified for 16 h in 30% methanolic KOH at room temperature for total sterol quanitification by GC or sterols were directly extracted with chloroform/methanol (4:1) and analysed by TLC to distinguish between free and esterified sterols or by GC for quantification of free sterols.

12. Squalene and Sterol Analysis

To quantify whole cell lipids and total lipids in lipid particles, samples were saponified prior to GC analysis. 125 $OD_{600}$ of cells were treated for 20 min at 100° C. in 0.5 N HCl and allowed to cool to room temperature. After that 3 g of KOH and 12.5 ml of methanol with pyrogallol (2 g/l) were added. For saponification the mixture was incubated for 2 h at 70° C. in a water bath. Hydrolysed esters were extracted in n-hexane. The non-saponified fraction was resuspended in 2 ml of n-hexane. Squalene and sterols were quantified by GC with squalene and cholesterol as internal standards. Squalene and Sterols were separated on a Hewlett-Packard 5890 gas chromatograph with a capillary column (25 m by 0.25 mm by 0.25 µm [film thickness]; Chrompack CPSil5) programmed from 150 to 250° C. The temperature was initially 150° C. for 2 min; it was then increased at 15° C./min to a final temperature of 250° C. at which it was held for 20 min. The linear velocity was 30 cm/s, helium was used as the carrier gas, and injections were run in the splitless mode. The injection volume was 1 µl. The area of each peak was calculated and related to one gram of cell dry weight. Each sample was measured in duplicate. Standards of ergosterol and squalene were used for identification.

Neutral lipids were extracted and quantified by a method of Sorger and Daum (J. Bacteriol. 184 (2002), 519-524). In detail, for the quantification of neutral lipids, extracts were applied to silica gel 60 plates and chromatograms were developed by using the solvent system light petroleum-diethyl ether-acetic acid (25:25:1, vol/vol/vol) for the first third of the distance. Then plates were dried briefly and further developed to the top of the plate with the solvent system light petroleum-diethyl ether (49:1, vol/vol). Neutral lipids were visualized by staining the thin layer plates with iodine vapour in a TLC-chamber. Quantification was carried out by densitometric scanning.

The standard culture procedure of strains of the yeast *Saccharomyces cerevisiae* for squalene and sterol analysis was:

Preculture: 20 ml of WMVIII medium in a 100 ml shaking flask are inoculated with 20 µl of the corresponding glycerol stock and cultivated for 48 h at 30° C. and 150 rpm.

Main culture: 50 ml of WMVIII medium in a 250 ml shaking flask with baffles are inoculated with 1% of the preculture and cultivated for 72 h at 30° C. and 150 rpm.

Example 1

Deletion of the Genes ARE1 and ARE2 in *S. cerevisiae* AH22ura3

The vector pUG6 (Güldener U, Heck S, Fiedler T, Beinhauer J D and Hegemann J H (1996). A new efficient gene disruption cassette for repeated use in budding yeast. Nucleic Acids Res 24 2519-24) has been used to delete the genes ARE1 and ARE2.

The deletion of both genes has been done successively by the same method. At first ARE1 has been deleted and afterwards ARE2. After plasmid preparation, a fragment of pUG6 has been amplified by PCR to obtain a tool consisting of loxP-kanMX-loxP. Primers have been constructed to fuse 5' and 3' sequences of ARE1 respec. ARE2 coding sequences to the loxP regions of pUG6 vector.

The resulting PCR product consists of a KanR gene, loxP sites and ARE1 respec. ARE2 homologous regions for the integrative transformation in *S. cerevisiae* AH22ura3. Homologous recombination in yeast leads to the deletion of the target sequence.

Resistance against G418 has been used for selection of positive clones. The ARE1 respec. ARE2 coding region has been deleted in this yeast strain. To prepare the strain for the deletion of further genes, the G418 resistance has been removed from the strain. For this purpose the strain has been transformed by pSH47 (Guldner et al., 1996). The vector carries the cre-recombinase to get rid of the KanR gene flanked by loxP sites.

To dispose pSH47 the strain has been counter selected on 5-FOA (5-Fluoroorotic acid) (1 g/L) agar plates. The resulting strain carries a deletion of both genes ARE1 and ARE2.

Example 2

Deletion of the Genes DGA1 and LRO1 in *S. cerevisiae* AH22ura3

The vector pUG6 (Guldner et al., 1996) has been used to delete the genes DGA1 and LRO1.

The deletion of both genes has been done successively by the same method. At first DGA1 has been deleted and afterwards LRO1. After plasmid preparation, a fragment of pUG6 has been amplified by PCR to obtain a tool consisting of loxP-kanMX-loxP. Primers have been constructed to fuse 5' and 3' sequences of the DGA1 respec. LRO1 coding sequences to the loxP regions of pUG6 vector.

The resulting PCR product consists of a KanR gene, loxP sites and DGA1 respec. LRO1 homologous regions for the integrative transformation in *S. cerevisiae* AH22ura3. Homologous recombination in yeast leads to the deletion of the target sequence.

Resistance against G418 has been used for selection of positive clones. The DGA1 respec. LRO1 coding region has been deleted in this yeast strain. To prepare the strain for the deletion of further genes, the G418 resistance has been removed from the strain. For this purpose the strain has been transformed by pSH47 (Guldner et al., 1996). The vector carries the cre-recombinase to get rid of the KanR gene flanked by loxP sites.

To dispose pSH47 the strain has been counterselected on 5-FOA (5-Fluoroorotic acid) (1 g/L) agar plates.

The resulting strain carries a deletion of both genes DGA1 and LRO1.

Example 3

Deletion of the Genes DGA1 and LRO1 in *S. cerevisiae* AH22ura3Are1are2

The vector pUG6 (Gul dner et al., 1996) has been used to delete the genes DGA1 and LRO1.

The deletion of both genes has been done successively by the same method. At first DGA1 has been deleted and afterwards LRO1. After plasmid preparation, a fragment of pUG6 has been amplified by PCR to obtain a tool consisting of loxP-kanMX-loxP. Primers have been constructed to fuse 5' and 3' sequences of the DGA1 respec. LRO1 coding sequences to the loxP regions of pUG6 vector.

The resulting PCR product consists of a KanR gene, loxP sites and DGA1 respec. LRO1 homologous regions for the integrative transformation in *S. cerevisiae* AH22ura3. Homologous recombination in yeast leads to the deletion of the target sequence.

Resistance against G418 has been used for selection of positive clones. The DGA1 respec. LRO1 coding region has been deleted in this yeast strain. To prepare the strain for the deletion of further genes, the G418 resistance has been removed from the strain. For this purpose the strain has been transformed by pSH47 (Guldner et al., 1996). The vector carries the cre-recombinase to get rid of the KanR gene flanked by loxP sites.

To dispose of pSH47 the strain has been counterselected on FOA (5-Fluoroorotic acid) (1 g/L) agar plates.

The resulting strain carries a quadruple deletion of the genes ARE1, ARE2, DGA1 and LRO1.

Example 4

Expression of t-HMG1 in Yeast Strains Resulting from Example 1 to 3 and AH22ura3 as Reference Strains, Using the Episomal Plasmid The DNA sequence for tHMG (Basson et al. (Mol. Cell. Biol. 8 (1988), 3793-3808)) was amplified by PCR from genomic DNA of *Saccharomyces cerevisiae* S288C. (Mortimer and Johnston (Genetics 113 (1986), 35-43)) with use of standard methods. The primers that are used in this case are the DNA oligomer tHMG-5' and tHMG-3'. The DNA-fragment that was obtained was introduced in cloning vector pUC19 (Yanisch-Perron et al. (1985): *Improved M13 phage cloning vectors and host strains: nucleotide sequences of the M13mp18 and pUC19 vectors*. In: *Gene*. Bd. 33, S. 103-119) after a Klenow treatment, and yielded vector pUC19-tHMG. After plasmid isolation and restriction of pUC 19-tHMG with endonucleases EcoRI and BamHI, the obtained fragment was introduced into yeast expression vector pPT2b (Lang and Looman (Appl. Microbiol. Biotechnol. 44 (1995), 147-156)), which also was treated with EcoRI and BamHI. The plasmid pPT2b-tHMG that was produced contains the truncated ADH1-promoter (Bennetzen and Hall (Yeast 7 (1982), 475-477)) and the TRP1-terminator (Tschumper G, Carbon J. Sequence of a yeast DNA fragment containing a chromosomal replicator and the TRP1 gene. Gene. 1980 July: 10(2)157-166), between which the tHMG-DNA fragment is found. A DNA section was isolated from vector pPT2b-tHMG via endonucleases EcoRV and NruI, and said DNA section contains the so-called medium-length ADH1-promoter, the tHMG gene and the TRP1-terminator. This DNA section was introduced into yeast vector YEp13 (Fischhoff et al. (Gene 27 (1984), 239-251)), which was treated with endonuclease SphI and a DNA polymerase.

YEpH2 has been transformed in *S. cerevisiae* AH22URA3are1are2, AH22URA3dga1lro1, AH22URA3are1are2dga1lro1 und AH22URA3. As reference plasmid YEp13 has been used.

Example 5

Chromosomal Integration and Overexpression of t-HMG1 in Yeast Strains Resulting from Example 1 to 3 and AH22ura3 as Reference Strains, Using the Chromosomal Integrative Plasmid YDpUHK3

The vector YEpH2 was treated with the endonucleases EcoRV and NruI. A DNA-fragment with the following areas was thus produced: a transcription-activating area from the tetracycline resistance gene (Sidhu and Bollon (10 (1990) 157-166)), the medium length ADH1-promoter, the tHMG and the TRP1-terminator (expression cassette). This DNA-fragment was introduced into vector YDpU (Berben et al. 1991 Berben G., Dumont J., Gilliquet V, Bolle P.-A. und Hilger F. (1991): "The YDp plasmids: a uniform set of vectors bearing versatile gene disruption cassettes for" *Saccharomyces cerevisiae"." Yeast* 7, 475-477), which was treated with StuI. Vector YDpUH2/12 that was thus produced was treated with endonuclease SmaI and ligated with a DNA-sequence that codes for a kanamycin resistance (Webster, T. D., Dickson, R. C. (1983) Direct selection of *Saccharomyces cerevisiae* resistant to the antiobiotic G418 following transformation with a DNA vector carrying the kanamycin-resistance gene of Tn903. Gene 26: 243-252). The construct that is produced (YDpUHK3) was treated with EcoRV. The yeast strain *Saccharomyces cerevisiae* AH22 was transformed with this construct. The transformation of the yeast with a linearized vector, as it is in this example, results in a chromosomal integration of the total vector at the URA3 gene locus. To eliminate the areas from the integrated vector that are not part of the expression cassette (*E. coli origin, E. coli-ampicillin* resistance gene, TEF-promoter and kanamycin resistance gene), transformed yeasts were subjected to a selection pressure by FOA selection (Boeke et al. (Methods in Enzymology 154 (1987), 164-175)) that promotes uracil-auxotrophic yeasts. The uracil-auxotrophic strain that is described in the selection bears the name AH22tH3ura8 and has the tHMG1-expression cassette as chromosomal integration in the URA3-gene.

The yeast strains indicated in table 1 have been evaluated on their squalene productivity/content. Thereto the strains have been cultivated for 72 h in WMVIII-Medium at 30° C. and 150 rpm shaking. After the cell disruption in 0.5 M boiling HCl the lipids were extracted with 2 times 20 ml n-hexane and analysed/quantified via GC/MS (please see item 12 for details). The following data has been obtained (Table 1).

TABLE 1

| Strain | Squalene [% per DW] |
| --- | --- |
| AH22tH3ura8 are1are2dga1lro1 | <0.1 |
| AH22tH3ura8 are1are2dga1 | 0.2 |
| AH22tH3ura8 are1are2lro1 | 1.0 |
| AH22tH3ura8 dga1lro1are2 | <0.1 |
| AH22tH3ura8 are1are2 | 11.2 |
| AH22tH3ura8 dga1lro1 | 2.1 |
| AH22tH3ura8 | 9.8 |
| AH22ura3 (Wild type, reference strain) | 0.1 |

Example 6

Deletion of the Gene FLD1 in *S. cerevisiae* AH22tH3Ura8 Are1are2

The vector pUG6 (Guldner et al., 1996) has been used to delete the gene FLD1.

After plasmid preparation, a fragment of pUG6 has been amplified by PCR to obtain a tool consisting of loxP-kanMX-loxP. Primers have been constructed to fuse 5' and 3' sequences of the FLD1 coding sequence to the loxP regions of the pUG6 vector.

The resulting PCR product consists of a KanR gene, loxP sites and FLD1 homologous regions for the integrative transformation in *S. cerevisiae* AH22tH3ura8 are1are2. Homologous recombination in yeast leads to the deletion of the target sequence.

Resistance against G418 has been used for selection of positive clones. The FLD1 coding region has been deleted in this yeast strain. To prepare the strain for the deletion of further genes, the G418 resistance has been removed from the strain. For this purpose the strain has been transformed by pSH47 (Guldner et al., 1996). The vector carries the cre-recombinase to get rid of the KanR gene flanked by loxP sites.

To dispose of pSH47 the strain has been counterselected on FOA (5-Fluoroorotic acid) (1 g/L) agar plates.

The resulting strain carries a triple deletion of the genes ARE1, ARE2 and FLD1 and is denoted AH22tH3ura8 are1are2fld1.

The yeast strains indicated in table 2 have been evaluated on their squalene productivity/content. Thereto the strains have been cultivated for 72 h in WMVIII-Medium at 30° C. and 150 rpm shaking. After the cell disruption in 0.5 M boiling HCl the lipids were extracted with 2 times 20 ml n-hexane and analysed/quantified via GC/MS (please see item 12 for details). The following data has been obtained (Table 2).

TABLE 2

| Strain | Squalene [% per DW] | Squalene/C-source [%] | Squalene/fermentation volume [g/L] |
| --- | --- | --- | --- |
| AH22tH3ura8 are1are2fld1 | 14.6 | 2.52 | 1.25 |
| AH22tH3ura8 are1are2 | 11.2 | 2.09 | 1.04 |
| AH22tH3ura8 | 9.8 | 1.81 | 0.91 |
| AH22ura3 (Wild type, reference strain) | 0.1 | <0.04 | <0.02 |

Example 7

Episomal Overexpression of the Genes SAK1 and HAP4 in Yeast Strains Resulting from Example 1 to 5

For the episomal overexpression of the genes SAK1 and HAP4 these genes were cloned into the expression vectors pFlat1 and pFlat3, respectively. Thereto the two genes were amplified from chromosomal DNA from strain *S. cerevisiae* S288 c with primers introducing a NotI restriction site at the 5' end and a XhoI restriction site at the 3' end. The resulting PCR fragments, as well as the vectors pFlat1 and pFlat3 were restricted with the restriction endo nucleases XhoI and NotI. The restricted PCR fragments and the linearized vectors were ligated resulting in vectors pFlat1-SAK1 and pFlat3-HAP4. These vectors carry a copy of the genes SAK1 and HAP4, respectively, adjacent to a constitutive version of the ADH1 promoter and to the TRP1 terminator in order to provide a strong constitutive expression of SAK1 and HAP4.

To construct plasmid pFlat3, the plasmid YEp24 was cut with SphI, and a 900 bp SphI fragment containing the ADH1 promoter and the TRP1 terminator spaced by a multiple cloning site of plasmid pUC19 was inserted from plasmid pPT2B. The multiple cloning site was extended by inserting a polylinker containing the restriction sites for NotI and XhoI. The resulting plasmid pFlat1 which carries a URA3 gene for selection was linearized by NcoI restriction, blunted by Klenow polymerase, and a blunt-ended BamHI fragment of YDpL containing the yeast LEU2 gene was integrated. The resulting vector was pFlat3.

The plasmids pFlat1-SAK1 and pFlat3-HAP4 and also the empty plasmids pFlat1 and pFlat 3 as control were transformed in the yeast strains resulting from example 1 to 6.

The yeast strains indicated in table 3 have been evaluated on their squalene productivity/content. Thereto the strains have been cultivated for 72 h in WMVIII-Medium at 30° C. and 150 rpm shaking. After the cell disruption in 0.5 M boiling HCl the lipids were extracted with 2 times 20 ml n-hexane and analysed/quantified via GC/MS (please see item 12 for details). The following data has been obtained (table 3).

TABLE 3

| Strain | Squalene [% per DW] |
|---|---|
| AH22tH3ura8 are1are2lro1 pFlat1-SAK1 pFlat3 | 3.5 |
| AH22tH3ura8 are1are2lro1 | 1.0 |
| AH22tH3ura8 are1are2dga1 pFlat1 pFlat3-HAP4 | 5.3 |
| AH22tH3ura8 are1are2dga1 pFlat1-SAK1 pFlat3-HAP4 | 7.6 |
| AH22tH3ura8 are1are2dga1 pFlat1-SAK1 pFlat3 | 5.1 |
| AH22tH3ura8 are1are2dga1 pFlat1 pFlat3 | 0.2 |
| AH22tH3ura8 dga1lro1 pFlat3-HAP4 | 3.8 |
| AH22tH3ura8 dga1lro1 pFlat3 | 2.1 |
| AH22tH3ura8 pFlat3-HAP4 | 28.7 |
| AH22tH3ura8 | 9.8 |
| AH22ura3 (Wild type, reference strain) | 0.1 |

Example 8

The neutral lipid composition of the constructed strains was evaluated via thin layer chromatography. Whole lipid extraction and thin layer chromatography was performed according to item 12. FIG. 1 shows the whole/neutral lipid composition of the wildtype strain AH22ura3, the strain with the deregulated HMG-CoA Reductase AH22tH3ura8 and the two double deletion strains AH22tH3ura8Δare1Δare2 and AH22tH3ura8Δdga1Δlro1. FIG. 1 indicates that the wildtype strain (AH22ura3, lane 1 and 2) produces very low amounts of squalene in comparison to the strains in lane 3 to 8, which express the deregulated HMG-CoA reductase and produce high amounts of squalene. The deletion of the genes encoding for the enzymes responsible for the formation of steryl esters (are1, are2) and triacylglycerols (dga1, lro1) results in a complete lack of these components in the corresponding strains (indicated by the black boxes in lane 5 to 8). The lipid components were identified via the standards squalene, cholesteryl-oleate, trioleate, oleate and ergosterol (not shown).

The invention claimed is:

1. An isolated genetically modified non-mammalian organism, wherein the activity of both ARE1 and ARE2 of acyl-CoA:sterol acyltransferase/sterol O-acyltransferase (EC 2.3.1.26) and/or activity of diacylglycerol acyltransferase/diacylglycerol O-acyltranferase (EC 2.3.1.20) and/or activity of lecithin cholesterol acyl transferase/phospholipid:diacylglycerol acyltransferase (EC 2.3.1.158) are reduced or abolished in comparison with a corresponding wildtype organism, and wherein the activity of 3-hydroxy-3-methyl-glutaryl-Coenzyme-A-reductacse (HMG-CoA-reductase) (EC1.1.1.34), is increased in comparison with the corresponding wildtype organism.

2. The organism of claim 1,
wherein at least a first lipid, accumulated in lipid particles of the corresponding wild type organism, is no longer synthesized, and
wherein a second lipid being different from the first lipid is accumulated in the lipid particles of the genetically modified organism,
wherein the second lipid is a prenol lipid.

3. The organism of claim 1, wherein one or two or all of the activities selected from the group consisting of SAM:C-24 sterol methyl transferase (EC 2.1.1.41), C-22 sterol desaturase (EC 1.14.14.-) and C-5 sterol desaturase (EC 1.14.21.6) is reduced or abolished in comparison with the corresponding wildtype organism.

4. The organism of claim 1, wherein one or two or all of the activities selected from the group consisting of squalene monooxygenase (EC1.14.99.7), sterol 14-demethylase (EC1.14.13.70) and 7-dehydrocholesterol reductase (EC1.3.1.21) is increased in comparison with the corresponding wildtype organism.

5. The organism of claim 1, wherein in addition to the modified activities of claim 1 the activities and/or amounts of heme-activated protein (HAP4p) and/or SNF1-activated kinase (SAKI p) are increased and/or wherein the activities and/or amounts of regenerating islet-derived 1pseudogene (REGI p) and/or lipid dropplets protein 1 (FLDI p) are decreased or abolished.

6. The organism of claim 2,
wherein the sterol is cholesterol, a cholesterol derivative, 7-dehydro-cholesterol, lanosterol, a lanosterol derivative, zymosterol, a zymosterol derivative, lathosterol, a lathosterol derivative, cucurbitacin, a cucurbatin derivative, episterol, a episterol derivative, teasterone, a teasterone derivative, castasterone, a castasterone derivative, typhasterol, a typhasterol derivative, cathasterone, a cathasterone derivative, cycloeucalenol, a cycloeucalenol derivative, sitosterol, a sitosterol derivative, isofucosterol, a isofucosterol derivative, fucosterol, a fucosterol derivative, gorgosterol, a gorgosterol derivative, ergosterol, an ergosterol derivative, stigmasterol or a stigmasterol derivative, or wherein the steroid is androsterone, an androsterone derivative, testosterone, a testosterone derivative, androstenediol, an androstenediol derivative, androstenedione, an androstenedione derivative, calusterone, a calusterone derivative, methandriol, a methandriol derivative, bolasterone, a bolasterone derivative, epiandrosterone, an epiandrosterone derivative, mestanolone, a mestanolone derivative, stanolone, a stanolone derivative, stenbolone, a stenbolone derivative, epitestosterone, an epitestosterone derivative, Cortisol, a Cortisol derivative, aldosterone, an aldosterone derivative, pregnenolone, a pregnenolone derivative, cortisone, a cortisone derivative, corticosterone, a corticosterone derivative, norethindrone, a norethindrone derivative, urocortisol or an urocortisol derivative.

7. The organism of claim 1,
wherein the organism is an eukaryotic organism.

8. The organism of claim 2, wherein the first lipid is a triacylglycerol and/or a sterylacylester and/or a waxester.

9. The organism of claim 2, wherein the second lipid is a triterpene.

10. The organism of claim 2, wherein the second lipid is selected from squalene or squalene derivative, and wherein the squalene derivative comprises one or more, additional methyl or ethyl groups bound to backbone carbon atoms instead of hydrogen atom(s) bound to backbone carbon atoms in squalene, and an acyl ester of a sterol lipid.

11. The organism of claim 2, wherein the prenol lipid is isoprenoid.

12. The organism of claim 1, wherein the eukaryotic organism is *Saccharomyces cerevisiae*.

* * * * *

SEQUENCE LISTING

<160> NUMBER OF SEQ ID NOS: 1

<210> SEQ ID NO 1
<211> LENGTH: 1578
<212> TYPE: DNA
<213> ORGANISM: Artificial Sequence
<220> FEATURE:
<223> OTHER INFORMATION: truncated HMG CoA-reductase

<400> SEQUENCE: 1

```
atggaccaat tggtgaaaac tgaagtcacc aagaagtctt ttactgctcc tgtacaaaag      60
gcttctacac cagtttttaac caataaaaca gtcatttctg gatcgaaagt caaaagttta     120
tcatctgcgc aatcgagctc atcaggacct tcatcatcta gtgaggaaga tgattcccgc     180
gatattgaaa gcttggataa gaaaatacgt cctttagaag aattagaagc attattaagt     240
agtggaaata caaaacaatt gaagaacaaa gaggtcgctg ccttggttat tcacggtaag     300
ttacctttgt acgctttgga gaaaaaatta ggtgatacta cgagagcggt tgcggtacgt     360
aggaaggctc tttcaatttt ggcagaagct cctgtattag catctgatcg tttaccatat     420
aaaaattatg actacgaccg cgtatttggc gcttgttgtg aaaatgttat aggttacatg     480
cctttgcccg ttggtgttat aggcccccttg gttatcgatg gtacatctta tcatatacca     540
atggcaacta cagagggttg tttggtagct tctgccatgc gtggctgtaa ggcaatcaat     600
gctggcggtg gtgcaacaac tgtttttaact aaggatggta tgacaagagg cccagtagtc     660
cgtttcccaa ctttgaaaag atctggtgcc tgtaagatat ggttagactc agaagaggga     720
caaaacgcaa ttaaaaagc ttttaactct acatcaagat ttgcacgtct gcaacatatt     780
caaacttgtc tagcaggaga tttactcttc atgagattta gaacaactac tggtgacgca     840
atgggtatga atatgatttc taaaggtgtc gaatactcat taaagcaaat ggtagaagag     900
tatggctggg aagatatgga ggttgtctcc gtttctggta actactgtac cgacaaaaaa     960
ccagctgcca tcaactggat cgaaggtcgt ggtaagagtg tcgtcgcaga agctactatt    1020
cctggtgatg ttgtcagaaa agtgttaaaa agtgatgttt ccgcattggt tgagttgaac    1080
attgctaaga atttggttgg atctgcaatg gctgggtctg ttggtggatt taacgcacat    1140
gcagctaatt tagtgacagc tgttttcttg gcattaggac aagatcctgc acaaaatgtt    1200
```

```
gaaagttcca actgtataac attgatgaaa gaagtggacg gtgatttgag aatttccgta    1260
tccatgccat ccatcgaagt aggtaccatc ggtggtggta ctgttctaga accacaaggt    1320
gccatgttgg acttattagg tgtaagaggc ccgcatgcta ccgctcctgg taccaacgca    1380
cgtcaattag caagaatagt tgcctgtgcc gtcttggcag gtgaattatc cttatgtgct    1440
gccctagcag ccggccattt ggttcaaagt catatgaccc acaacaggaa acctgctgaa    1500
ccaacaaaac ctaacaattt ggacgccact gatataaatc gtttgaaaga tgggtccgtc    1560
acctgcatta aatcctaa                                                  1578
```